United States Patent
Seki et al.

(10) Patent No.: US 7,912,530 B2
(45) Date of Patent: Mar. 22, 2011

(54) MAGNETIC DETECTION COIL AND APPARATUS FOR MEASUREMENT OF MAGNETIC FIELD

(75) Inventors: Yusuke Seki, Tokyo (JP); Akihiko Kandori, Tokyo (JP)

(73) Assignee: Hitachi High-Technologies Corporation, Toyko (JP)

( * ) Notice: Subject to any disclaimer, the term of this patent is extended or adjusted under 35 U.S.C. 154(b) by 636 days.

(21) Appl. No.: 11/545,461

(22) Filed: Oct. 11, 2006

(65) Prior Publication Data

US 2007/0085534 A1 Apr. 19, 2007

(30) Foreign Application Priority Data

Oct. 14, 2005 (JP) .................................. 2005-300991

(51) Int. Cl.
*A61B 5/00* (2006.01)

(52) U.S. Cl. ........ 600/409; 600/407; 600/424; 324/307; 324/244; 324/248; 324/260

(58) Field of Classification Search .................. 600/409, 600/410; 324/307, 244, 248, 260
See application file for complete search history.

(56) References Cited

U.S. PATENT DOCUMENTS

| | | | | |
|---|---|---|---|---|
| 5,458,142 A | * | 10/1995 | Farmer et al. | 600/409 |
| 5,656,937 A | * | 8/1997 | Cantor | 324/248 |
| 5,668,472 A | * | 9/1997 | Ohyu | 324/248 |
| 5,825,183 A | * | 10/1998 | Morooka et al. | 324/248 |
| 5,891,031 A | * | 4/1999 | Ohyu | 600/409 |
| 6,337,567 B1 | * | 1/2002 | Lee et al. | 324/248 |
| 6,424,853 B1 | * | 7/2002 | Tsukada et al. | 600/409 |
| 6,462,540 B1 | * | 10/2002 | Kandori et al. | 324/248 |
| 7,002,341 B2 | * | 2/2006 | Baudenbacher et al. | 324/248 |

FOREIGN PATENT DOCUMENTS

| | | |
|---|---|---|
| JP | 03-025375 | 6/1989 |
| JP | 04-005589 | 4/1990 |
| JP | 04-005590 | 4/1990 |
| JP | 06-109820 | 9/1992 |
| JP | 9-84777 | 9/1995 |
| JP | 09-166653 | 12/1995 |
| JP | 2000-147078 | 5/2000 |

OTHER PUBLICATIONS

Office Action from Japanese Patent Office, dated Mar. 9, 2010, in Japanese.
Office Action from Japanese Patent Office for Japanese Patent Application JP-2005-300991, dated May 25, 2010, in Japanese.

* cited by examiner

*Primary Examiner* — Ruth S Smith
*Assistant Examiner* — Mark Remaly
(74) *Attorney, Agent, or Firm* — Stites & Harbison, PLLC; Juan Carlos A. Marquez, Esq.

(57) ABSTRACT

A magnetic detection coil is provided, which includes a plurality of differential coils. Each differential coil is made of one of superconductors and metallic materials. The differential coils having mutually different loop directions are arranged in parallel at a spatially predetermined distance apart and mutually electrically connected in series. Each differential coil is one of a first-order differential coil and a second-order differential coil.

6 Claims, 18 Drawing Sheets

MAGNETIC DETECTION COIL AND APPARATUS FOR MEASUREMENT OF MAGNETIC FIELD

CLAIM OF PRIORITY

The present application claims priority on Japanese application JP2005-300991 filed on Oct. 14, 2005, the content of which is hereby incorporated by reference into this application.

BACKGROUND OF THE INVENTION

The present invention relates to an apparatus for measurement of biomagnetism which employs magnetic detection coils and superconducting quantum interference devices.

An apparatus for measurement of biomagnetism, which is used for magnetocardiography and magnetoencephalography, has so far employed a technique that a magnetic detection coil made of superconducting wires detects magnetic signals generated by an organism to transmit to a superconducting quantum interference device (hereinafter referred to as SQUID). A SQUID has a superconductor ring with a Josephson junction, in which a voltage between both ends of the Josephson junction cyclically varies with a period of $\Phi_0=h/2e$ (Wb) according to a magnetic flux penetrating the SQUID.

It has been a typical technique in magnetocardiography and magnetoencephalography that a magnetic detection coil made of superconducting wires detects magnetic signals generated by a measurement object as a magnetic flux, which is transmitted to a SQUID. The magnetic detection coil helps to eliminate noise due to environmental magnetic fields to increase a Signal/Noise (S/N) ratio.

FIG. 17 is a schematic diagram illustrating architecture of a Flux Locked Loop (FLL) circuit in a typical apparatus for measurement of a magnetic field.

In an FLL circuit 1700, current produced by a magnetic flux penetrating a magnetic detection coil 1701 flows through the magnetic detection coil 1701 and an input coil 1702. Accordingly, the input coil 1702 creates a magnetic flux, which is transmitted to a SQUID 1703. The SQUID 1703, which has a superconducting ring with a Joesphson joint, is supplied a bias current by a bias current source 1705. A voltage between both ends of the SQUID 1703 cyclically varies with a period of $\Phi_0=h/2e$ (Wb) according to a magnetic flux penetrating the SQUID 1703. In the FLL circuit 1700, a feedback circuit, which includes a preamp 1706, an integrator 1707, a feedback resistor 1708 and a feedback coil 1704, is provided in a rear stage of the SQUID 1703. The feedback coil 1704 feeds back a magnetic flux so as to cancel a change in the magnetic flux penetrating the SQUID 1703.

It is possible to obtain current flowing through the feedback coil 1704 by measuring a potential difference between both ends of the feedback resistor 1708. The magnetic flux penetrating the SQUID 1703 can be calculated based on this current value.

A circuit which has the architecture described above is called FLL circuit. The FLL circuit 1700 provides an output voltage proportional to the magnetic field detected by the magnetic detection coil 1701.

Description is given of a typical magnetic detection coil used for an apparatus for measurement of biomagnetism with reference to FIG. 18.

FIGS. 18A to 18E are schematic diagrams illustrating magnetic detection coils used for an apparatus for measurement of biomagnetism.

FIG. 18A shows a zero-order differential magnetic detection coil (magnetometer), FIG. 18B a first-order differential magnetic detection coil, FIG. 18C a second-order differential magnetic detection coil, FIG. 18D a zero-order differential magnetic detection coil formed on a thin film substrate and FIG. 18E a first-order differential magnetic detection coil formed on a thin film substrate.

As shown in these drawings, a magnetic detection coil typically employs architecture in which superconducting wires are wound around a cylindrical bobbin or the other architecture in which a thin film is formed on a substrate.

As shown in FIG. 18A, a zero-order differential magnetic detection coil 181 has a coil 181a which is made of a bobbin 1811 wound by one turn of superconducting wire. A magnetic flux $\Phi_M$ in the following equation (1) detected by the zero-order differential magnetic detection coil 181 is represented by a magnetic flux $\Phi_{181a}$ penetrating the coil 181a as follows:

$$\Phi_M = \Phi_{181a} \quad (1)$$

Because the magnetic flux $\Phi_M$ is equivalent to the magnetic flux $\Phi_{181a}$ penetrating the coil 181a, the zero-order differential magnetic detection coil 181 is able to obtain magnetic signals greater than the first-order and second-order differential magnetic detection coils to be described later. However, the zero-order differential magnetic detection coil does not decrease an effect of environmental magnetic fields at all, directly experiencing noise due to the environmental magnetic fields. Accordingly, the zero-order differential magnetic detection coil 181 is usually used in a magnetically shielded room.

In this specification, a distance between centers of coils is referred to as "center-to-center distance".

Given the magnetic flux $\Phi_M$ shown in FIG. 18A is a positive magnetic signal, current flows through the zero-order differential magnetic detection coil 181 in a direction of a fine arrow, which is drawn along the coil. Hereinafter, a signal representative of a magnetic flux pointing upward is defined as a positive magnetic signal. A direction of current, which flows through a coil when a positive magnetic signal is detected, is represented by a fine arrow.

As shown in FIG. 18B, a first-order differential magnetic detection coil 182 has coils 182a and 182b. The coil 182a has one turn of superconducting wire, which is wound around a bobbin 1821 in a first direction. The coil 182b has one turn of superconducting wires which is wound around the bobbin 1821 in a second direction opposite to the first direction, lying a predetermined distance vertically apart from the coil 182a. A magnetic flux $\Phi_{G1}$ in the following equation (2) detected by the first-order differential magnetic detection coil 182 is represented by a magnetic flux $\Phi_{182a}$ penetrating the coil 182a and a magnetic flux $\Phi_{182b}$ penetrating the coil 182b as follows:

$$\Phi_{G1} = \Phi_{182a} - \Phi_{182b} \quad (2)$$

The reason why the magnetic flux $\Phi_{182b}$ has a minus value is that the coil 182b is wound in the opposite direction.

It should be noted that taking a difference is referred to as "differentiating", taking a first-order difference as "first-order differentiating" and taking a second-order difference as "second-order differentiating" in this specification.

The coil 182a is located proximity to a detection object and the coil 182b is located relatively away from it. Because environmental magnetic fields of spatial uniformity are cancelled, it is possible to detect only a magnetic flux deriving from the detection object.

It should be noted that a vertical direction is meant to represent a direction perpendicular to a plane including a coil and a horizontal direction is meant to represent a direction in parallel with this plane. In this connection, it may be possible to allow the vertical direction to coincide with a direction of measurement of a magnetic field.

As shown in FIG. 18C, a second-order differential magnetic detection coil 183 has coils 183a, 183b and 183c. The coil 183a has one turn of superconducting wire wound around a bobbin 1831 in a first direction. The coil 183b has two turns of superconducting wire wound around the bobbin 1831 in a second direction opposite to the first direction, lying a predetermined distance vertically apart from the coil 183a. The coil 183c has one turn of superconducting wire wound around the bobbin 1831 in the first direction, lying a predetermined distance vertically apart from the coil 183b. A magnetic flux $\Phi_{G2}$ in the following equation (3) detected by the second-order differential magnetic detection coil 183 is represented by a magnetic flux $\Phi_{183a}$ penetrating the coil 183a, a magnetic flux $\Phi_{183b}$ penetrating the coil 183b and a magnetic flux $\Phi_{183c}$ penetrating the coil 183c as follows:

$$\Phi_{G2}=\Phi_{183a}-2\Phi_{183b}+\Phi_{183c} \qquad (3)$$

As described above, the second-order differential magnetic detection coil 183 differentiates magnetic fluxes in two steps in a vertical direction, thereby decreasing an effect due to both environmental magnetic fields of spatial uniformity and environmental magnetic fields having a first-order gradient. As a result, the second-order differential magnetic detection coil 183 is able to decrease the effect of the environmental magnetic fields more than the first-order differential magnetic detection coil 182 which is only able to decrease the effect of the environmental magnetic fields of spatial uniformity. When a magnetic signal is included in the magnetic flux $\Phi_{183b}$ penetrating the coil 183b and the magnetic flux $\Phi_{183c}$ penetrating the coil 183c, a magnetic signal detected by the second-order differential magnetic detection coil 183 will decrease. It is understood that the higher order a differential magnetic detection coil possesses, the less effect of environmental magnetic fields will exist. However, a detected magnetic signal will decrease accordingly. In this way, a tradeoff study is necessary to solve the irreconcilable situations described above. A magnetometer, a first-order differential magnetic detection coil, or a second-order differential magnetic detection coil has been so far typically used for biomagnetism in conjunction with a magnetically shielded room according to magnitude of environmental magnetic fields.

There is a technique to use a superconducting thin film instead of superconducting wires for a magnetic detection coil. FIG. 18D shows a zero-order differential magnetic detection coil 184, in which a superconducting thin film is formed on a substrate 1841. A magnetic flux $\Phi_{184a}$ detected by a coil 184a is transmitted to a SQUID 1842 formed on the same substrate 1841. FIG. 18E shows a first-order differential magnetic detection coil 185, in which coils 185a and 185b having directions opposite to each other are formed on a substrate 1851. A difference $\Phi_{185a}-\Phi_{185b}$ between a magnetic flux $\Phi_{185a}$ detected by the coil 185a and a magnetic flux $\Phi_{185b}$ detected by the coil 185b is transmitted to a SQUID 1852 formed on the same substrate 1851. An advantage of using the superconducting thin film is that it is possible to determine and materialize an accurate area of a magnetic detection coil.

Several types of arrangements for magnetic detection coils have been proposed taking into account characteristic features of the differential coils described above. As an example, a technique has been proposed, in which plural types of magnetic detection coils having different differential orders are placed at a measurement point so as to calculate and estimate magnetic field sources or a distribution of the magnetic field sources in an organism. Patent document No. 1: Japanese Published Patent Application 09-084777 (claim 1, paragraph 0015, FIG. 1).

However, as shown in FIGS. 18A to 18C, there have been limited arrangements in which only a magnetic field differentiated in a certain direction is detected. These arrangements have a problem that when environmental magnetic fields are strong because a magnetically shielded room is not available, for example, it is not possible to adequately reduce an effect of them. One possible technique is to increase order for a differential magnetic detection coil so as to decrease this effect. Although the effect can be decreased by this technique, it is inevitably accompanied by a reduction in a magnetic signal to be detected.

A magnetic detection coil using a superconducting thin film has a problem that it is intrinsically difficult to form a coil three-dimensionally.

In addition, it appears to be unproductive to combine these two types of coils, because magnetic detection coils with three-dimensional structure as shown in FIGS. 18A to 18C and magnetic detection coils formed on a superconducting thin film as shown in FIGS. 18D and 18E are different from each other in terms of usage, structure and manufacturing processes.

SUMMARY OF THE INVENTION

In view of the problems described above, the present invention has an object to provide a magnetic detection coil and an apparatus for measurement of a magnetic field, which acquire increased S/N ratios as a result of not only avoiding a decrease in detection sensitivity for magnetic signals but also decreasing an effect due to environmental magnetic fields.

It is an aspect of the present invention to provide a magnetic detection coil including a plurality of differential coils. Each differential coil is made of one of a superconductor and metallic materials. The differential coils having mutually different loop directions are arranged in parallel at spatially predetermined intervals and mutually electrically connected. Each differential coil is one of a first-order differential coil and a second-order differential coil.

The present invention provides the magnetic detection coil and the apparatus for measurement of a magnetic field, which has the advantage of increased S/N ratios as a result of not only avoiding a decrease in detection sensitivity for magnetic signals but also decreasing an effect due to environmental magnetic fields.

DESCRIPTION OF THE PREFERRED EMBODIMENTS

Figure 1:
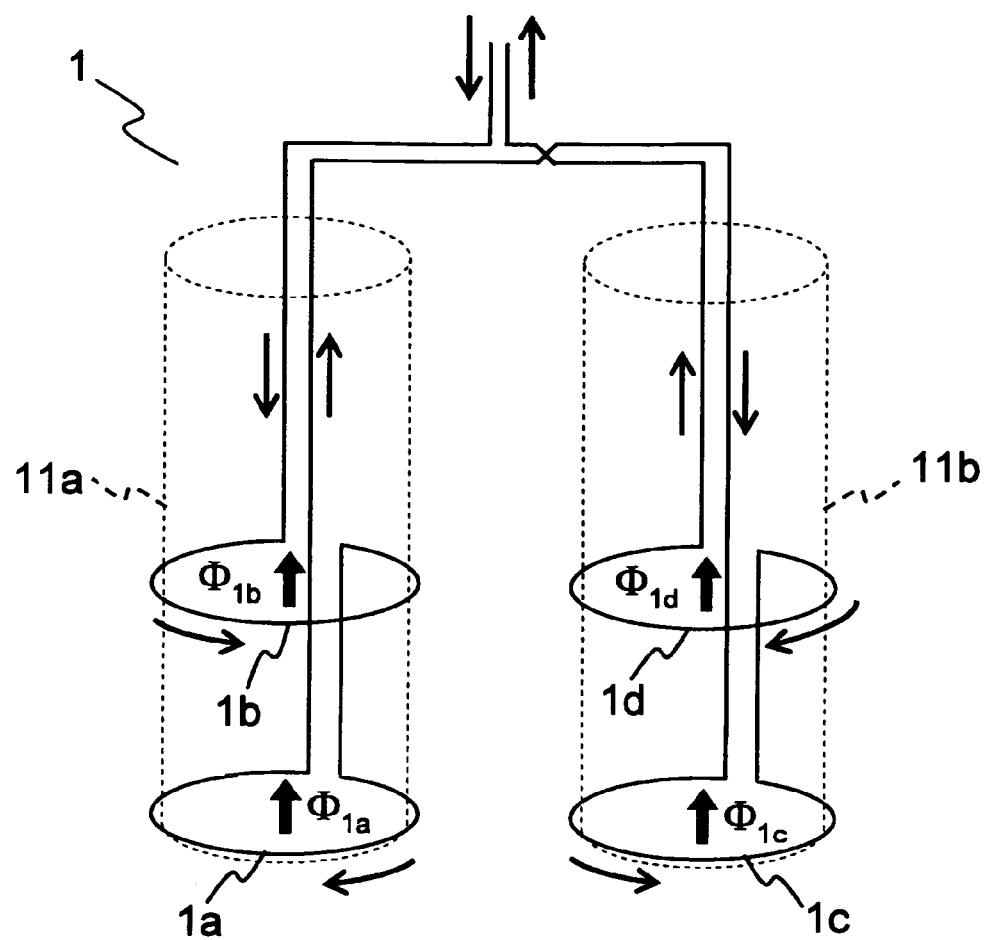
FIG. 1 is a perspective view showing a magnetic detection coil according to an embodiment (case 1 of the present invention).

An embodiment of the present invention is now described in detail with reference to the drawings. In the drawings referenced hereinafter, items having a same function are given a same reference number.

Low-temperature superconducting materials or high-temperature superconducting materials can be used as superconducting materials for a magnetic detection coil used in an apparatus described in the following embodiment. A low-temperature superconducting material, which has a low superconductor transition temperature, works as a superconductor in a low-temperature (liquid helium temperature) environment. In contrast, a high-temperature superconducting material, which has a high superconductor transition temperature, works as a superconductor in a high-temperature (liquid nitrogen temperature) environment. It may be possible to alternatively adopt a superconducting material having a superconductor transition temperature between the liquid helium temperature and the liquid nitrogen temperature or a superconducting material having a higher superconductor transition temperature than the liquid nitrogen temperature. It is understood that materials having high electric conductivity such as copper can be used for a member of a magnetic detection coil.

a. Magnetic Detection Coil—1

FIG. 1 is a perspective view showing a magnetic detection coil according to an embodiment.

A magnetic detection coil 1 includes coils 1a, 1b, 1c and 1d, and bobbins 11a and 11b. The coil 1a is formed by one turn of superconducting wire wound around the bobbin 11a in a first direction. The coil 1b is formed by one turn of superconducting wire wound around the bobbin 11a in a second direction opposite to the first direction, lying vertically a predetermined distance apart from the coil 1a. The coil 1c is formed by one turn of superconducting wire wound around the bobbin 11b in the second direction, which is positioned horizontally a predetermined distance from the coil 1a. The coil 1d is formed by one turn of superconducting wire wound around the bobbin 11b in the first direction, lying vertically a predetermined distance apart from the coil 1c. To summarize, the magnetic detection coil 1 is made of one continuous wire. The coils 1a and 1c are located in a same plane and the coils 1b and 1d are located in a same plane. In other words, first-order differential coils are arranged in parallel spaced a predetermined distance apart. A magnetic flux $\Phi_{P1}$ in the following equation (4) detected by the magnetic detection coil 1 is represented by a magnetic flux $\Phi_{1a}$ penetrating the coil 1a, a magnetic flux $\Phi_{1b}$ penetrating the coil 1b, a magnetic flux $\Phi_{1c}$ penetrating the coil 1c and a magnetic flux $\Phi_{1d}$ penetrating the coil 1d as follows:

$$\Phi_{P1}=(\Phi_{1a}-\Phi_{1b})-(\Phi_{1c}-\Phi_{1d}) \tag{4}$$

The magnetic detection coil 1 according to this embodiment is a magnetic detection coil which has a first-order differential function not only in an axial direction (vertical direction) with respect to the bobbin 11a (first term) and the bobbin 11b (second term) but also in a horizontal direction. Because the magnetic detection coil 1 detects magnetic signals which are first-order differentiated in both vertical and horizontal directions, it is possible to reduce an effect due to environmental magnetic fields more than the first-order differential magnetic detection coil 182 shown in FIG. 18B.

b. Magnetic Detection Coil—2

Figure 2:
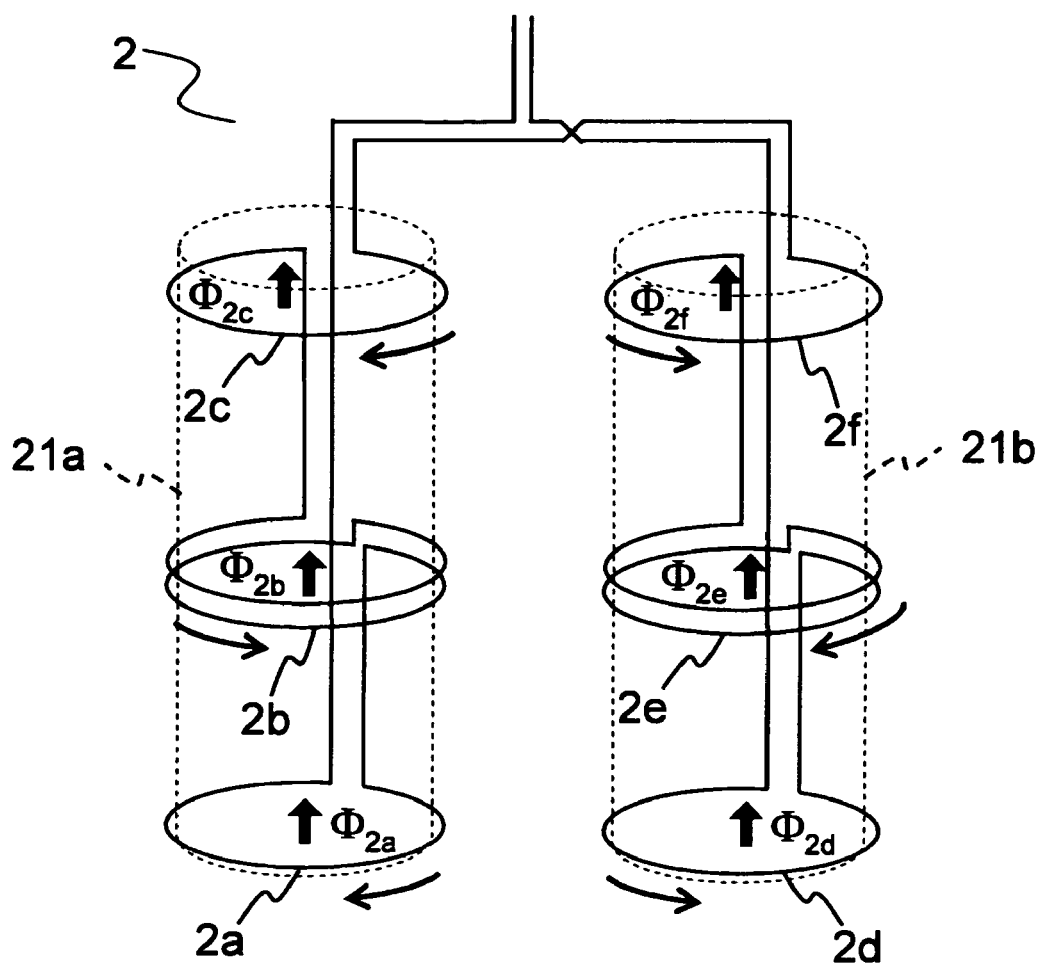
FIG. 2 is a perspective view showing a magnetic detection coil according to an embodiment (case 2 of the present invention).

FIG. 2 is a perspective view showing a magnetic detection coil according to an embodiment.

A magnetic detection coil 2 includes coils 2a, 2b, 2c, 2d, 2e and 2f, and bobbins 21a and 21b. The coil 2a is formed by one turn of superconducting wire wound around the bobbin 21a in a first direction. The coil 2b is formed by two turns of superconducting wire wound around the bobbin 21a in a second direction opposite to the first direction, lying vertically a predetermined distance apart from the coil 2a. The coil 2c is formed by one turn of superconducting wire wound around the bobbin 21a in the first direction, lying vertically a predetermined distance apart from the coil 2b. The coil 2d is formed by one turn of superconducting wire wound around the bobbin 21b in the second direction, which is positioned horizontally a predetermined distance from the coil 2a. The coil 2e is formed by two turns of superconducting wire wound around the bobbin 21b in the first direction, lying vertically a predetermined distance apart from the coil $2d$. The coil $2f$ is formed by one turn of superconducting wire wound around the bobbin $21b$ in the second direction, lying vertically a predetermined distance apart from the coil $2e$. To summarize, the magnetic detection coil 2 is made of one continuous wire. Both pair of the coils $2a$ and $2d$, the coils $2b$ and $2e$, and the coils $2c$ and $2f$ are located on a same plane, respectively. In other words, second-order differential coils are arranged in parallel spaced a predetermined distance apart. A magnetic flux $\Phi_{P2}$ in the following equation (5) detected by the magnetic detection coil 2 is represented by a magnetic flux $\Phi_{2a}$ penetrating the coil $2a$, a magnetic flux $\Phi_{2b}$ penetrating the coil $2b$, a magnetic flux $\Phi_{2c}$ penetrating the coil $2c$, a magnetic flux $\Phi_{2d}$ penetrating the coil $2d$, a magnetic flux $\Phi_{2e}$ penetrating the coil $2e$ and a magnetic flux $\Phi_{2f}$ penetrating the coil $2f$ as follows:

$$\Phi_{P2} = (\Phi_{2a} - 2\Phi_{2b} + \Phi_{2c}) - (\Phi_{2d} - 2\Phi_{2e} + \Phi_{2f}) \quad (5)$$

The magnetic detection coil 2 according to this embodiment is one which has not only a second-order differential function in an axial direction (vertical direction) with respect to the bobbin $21a$ (first term) and the bobbin $21b$ (second term), but also a first-order differential function in a horizontal direction. Because the magnetic detection coil 2 detects magnetic signals which are second-order differentiated in the vertical direction and first-order differentiated in the horizontal direction, it is possible to reduce an effect due to environmental magnetic fields more than the second-order differential magnetic detection coil 183 shown in FIG. 18C.

It should be noted that a circular shape of the coil used in the magnetic detection coils shown in FIG. 1 and FIG. 2 is an example and it may be possible to alternatively select other shapes such as a polygonal shape.

c. Simulation Results

Description is given of advantages in terms of signal strength of magnetic signals (hereinafter referred to as "signal strength") detected by the magnetic detection coils according to the embodiments with reference to FIGS. 3 to 7.

A current dipole of a cardiac muscle of a typical thirty-week unborn child is assumed as a magnetic signal source in a simulation. (See A. Kandori, T. Miyashita, and K. Tsukada, "A vector fetal magnetocardiogram system with high sensitivity" Review of Scientific Instruments USA, December 1999, Volume 70, P.4702). Assuming that current concentrates at one point $r_0 = (0, 0, -z_0)$, a current dipole Q is defined by the following equation (6), where $J(r)$ is a current density at $r = (x, y, z)$ (See "Basic mathematical and electromagnetic concepts of the biomagnetic inverse problem" J. Sarvas, Physics in Medicine and Biology, January 1987, Volume 32 P.11).

$$J(r) = \delta(r - r_0) Q \quad (6)$$

$\delta(r-r_0)$ represents a delta function. A magnetic flux density $B(r)$ due to the current dipole Q is represented by the following equation (7).

$$B(r) = (\mu_0/4\pi) Q \times (r - r_0)/|r - r_0|^3 \quad (7)$$

Values are set as follows: $Q = (0, 250, 0)$ (nA·m), $z_0 = 80$ (mm) and a vertical distance between neighboring coils is equal to 50 (mm). $z_0$ represents a distance from the magnetic detection coil to the current dipole Q, which is hereinafter meant to denote a distance between a plane made by a coil of the magnetic detection coil and the current dipole Q. $\mu_0 = 4\pi/10^7$ is a magnetic permeability in a vacuum condition.

Figure 3A:
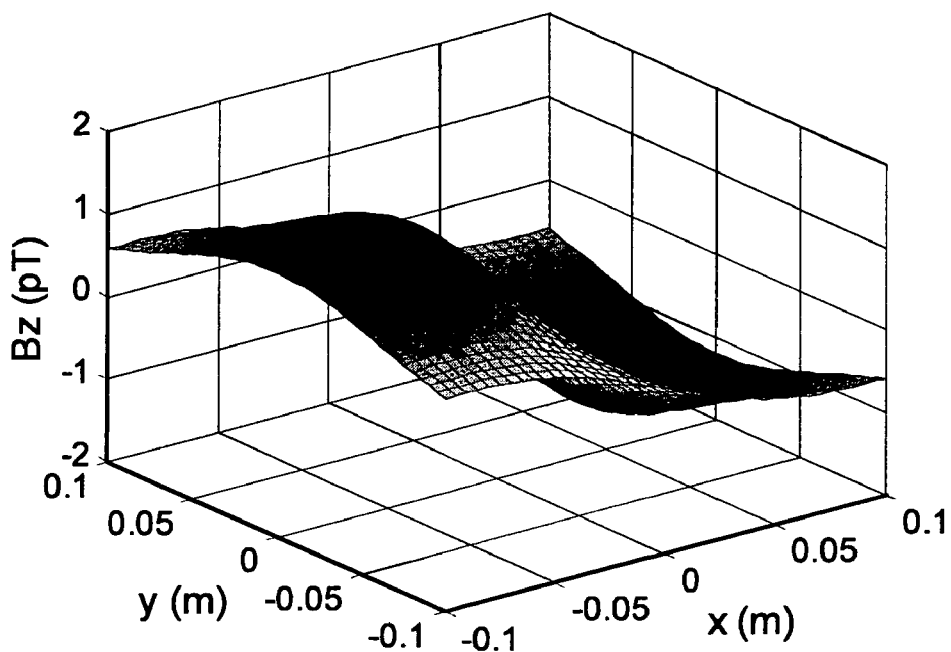
FIG. 3A is a graph showing simulation results for a distribution of signal strength detected by a zero-order differential magnetic detection coil shown in FIG. 18A.
Figure 3B:
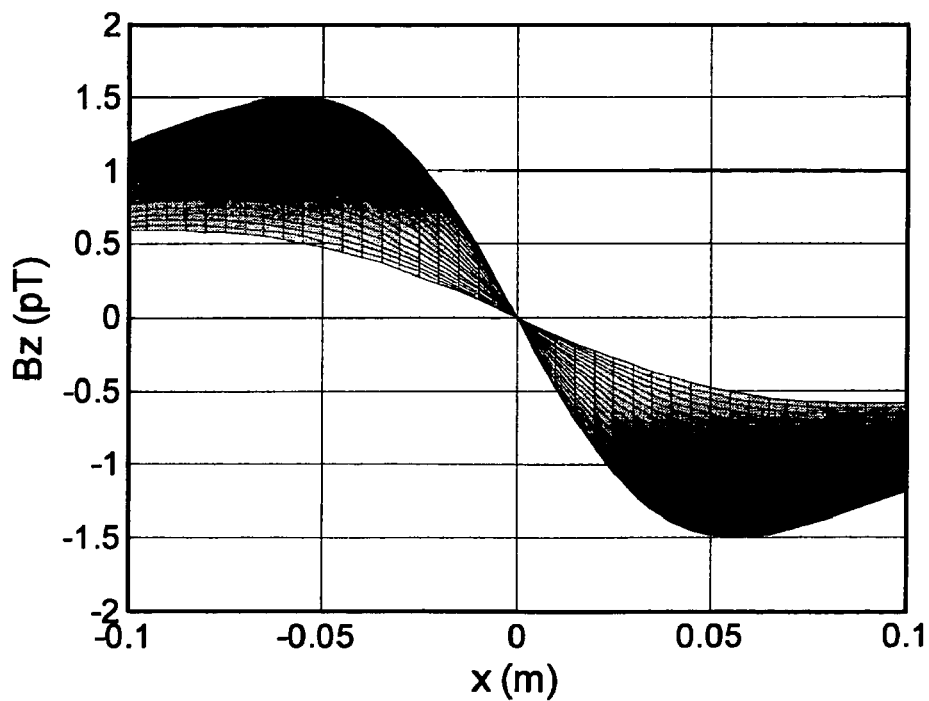
FIG. 3B is a graph showing a projection of FIG. 3A on an x-$B_z$ plane.
Figures 18A, 18B, 18C:
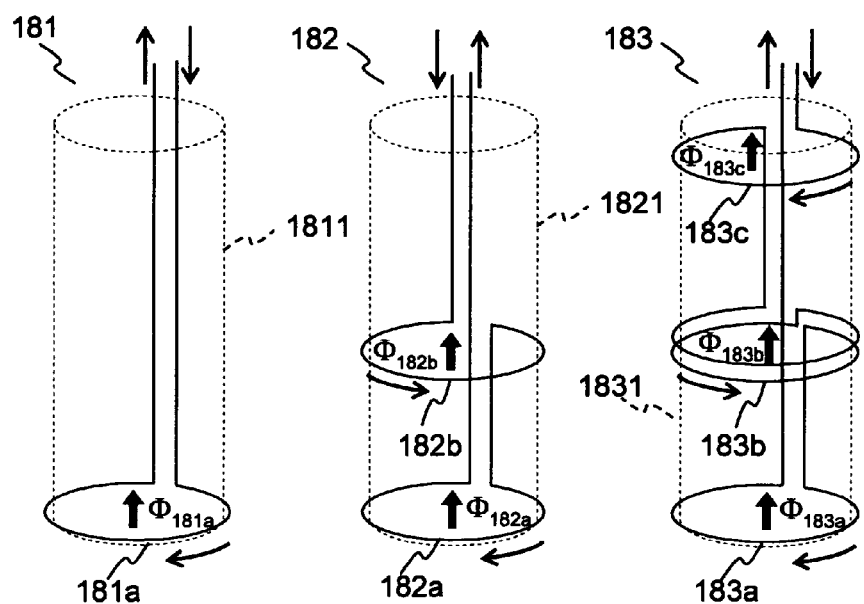
FIG. 18A shows a zero-order differential magnetic detection coil (magnetometer).
FIG. 18B shows a first-order differential magnetic detection coil.
FIG. 18C shows a second-order differential magnetic detection coil.

A description is given of signal strength detected by a zero-order differential magnetic detection coil with reference to FIG. 3A and FIG. 3B along with FIG. 18A.

FIG. 3A is a graph showing a distribution of signal strength detected by a zero-order differential magnetic detection coil shown in FIG. 18A. FIG. 3B is a graph showing a projection of FIG. 3A on an x-$B_z$ plane.

In FIGS. 3A and 3B, a central position of the coil $181a$ of the zero-order differential magnetic detection coil 181 (see FIG. 18A) is set equal to $(x, y, 0)$ (m). This means that the signal strength is equivalent to a distribution $B_z(x, y, 0)$, which is a distribution of a z-component $B_z(r)$ of the magnetic flux density $B(r)$ of the equation (7) on an xy-plane. Partially differentiating $B_z(x, y, 0)$ with respect to x, which has maximum and minimum values, a distribution of magnetic field generated by the current dipole Q is represented by the following equation (8).

$$\partial B_z/\partial x = (\mu Q/4\pi)(\sqrt{2x} + \sqrt{(y^2 + z_0^2)})(\sqrt{2x} - \sqrt{(y^2 + z_0^2)})/(x^2 + y^2 + z_0^2)^{5/2} \quad (8)$$

According to the equation (8), $B_z$ takes a maximum value at $x = \sqrt{(y^2 + z_0^2)/2}$ and a minimum value at $x = -\sqrt{(y^2 + z_0^2)/2}$, respectively.

Substituting $x = -\sqrt{(y^2 + z_0^2)/2}$ and $x = \sqrt{(y^2 + z_0^2)/2}$ for $B_z(x, y, 0)$, equations (9) and (10) are respectively obtained.

$$B_z(-\sqrt{(y^2+z_0^2)/2}, y, 0) = (\mu Q/4\pi)(2/3\sqrt{3})/(y^2 + z_0^2) \quad (9)$$

$$B_z(\sqrt{(y^2+z_0^2)/2}, y, 0) = -(\mu Q/4\pi)(2/3\sqrt{3})/(y^2 + z_0^2) \quad (10)$$

According to the equations (9) and (10), $B_z(x, y, 0)$ takes a maximum value $B_z^{max}$ at $P_{max} = (-z_0/\sqrt{2}, 0, 0)$ and a minimum value $B_z^{min}$ at $P_{min} = (z_0/\sqrt{2}, 0, 0)$. Signal strengths are represented by equations (11) and (12), respectively.

$$B_z^{max} = (\mu Q/4\pi)(2/3\sqrt{3})/z_0^2 \quad (11)$$

$$B_z^{min} = -(\mu_0 Q/4\pi)(2/3\sqrt{3})/z_0^2 \quad (12)$$

Reading out signal strengths at $P_{max}$ and $P_{min}$ from FIG. 3B, it is known that $B_z^{max}$ and $B_z^{min}$ are equal to 1.5 pT and −1.5 pT, respectively.

A center-to-center distance d of the points $P_{max}$ and $P_{min}$ is represented by the following equation.

$$d = \sqrt{2} z_0 \quad (13)$$

Figure 4A:
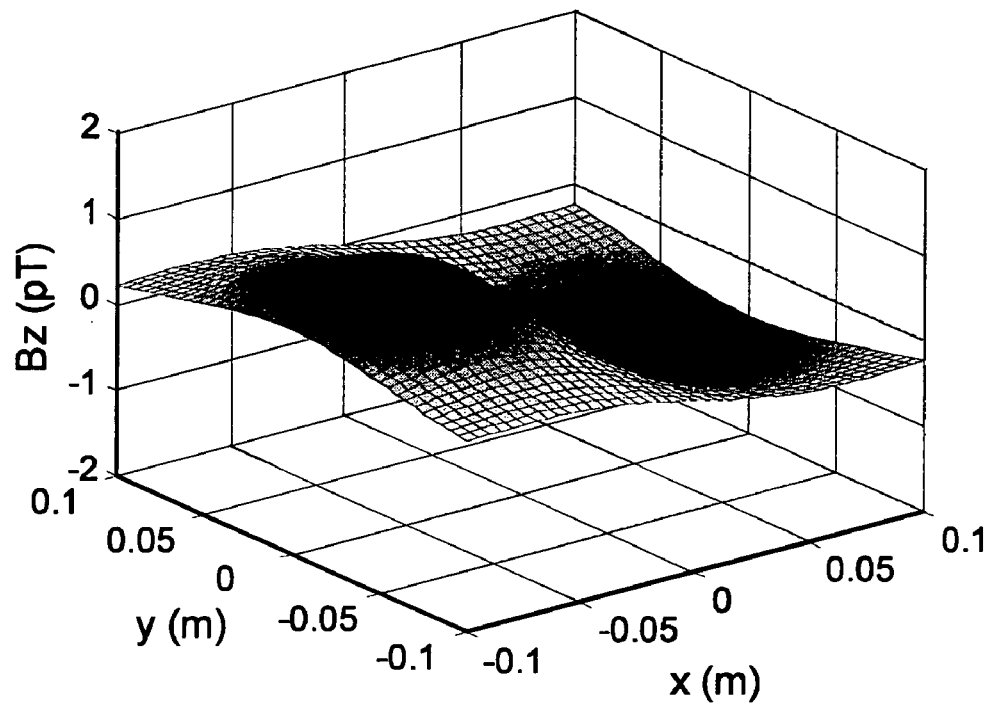
FIG. 4A is a graph showing simulation results for a distribution of signal strength detected by a first-order differential magnetic detection coil shown in FIG. 18B.
Figure 4B:
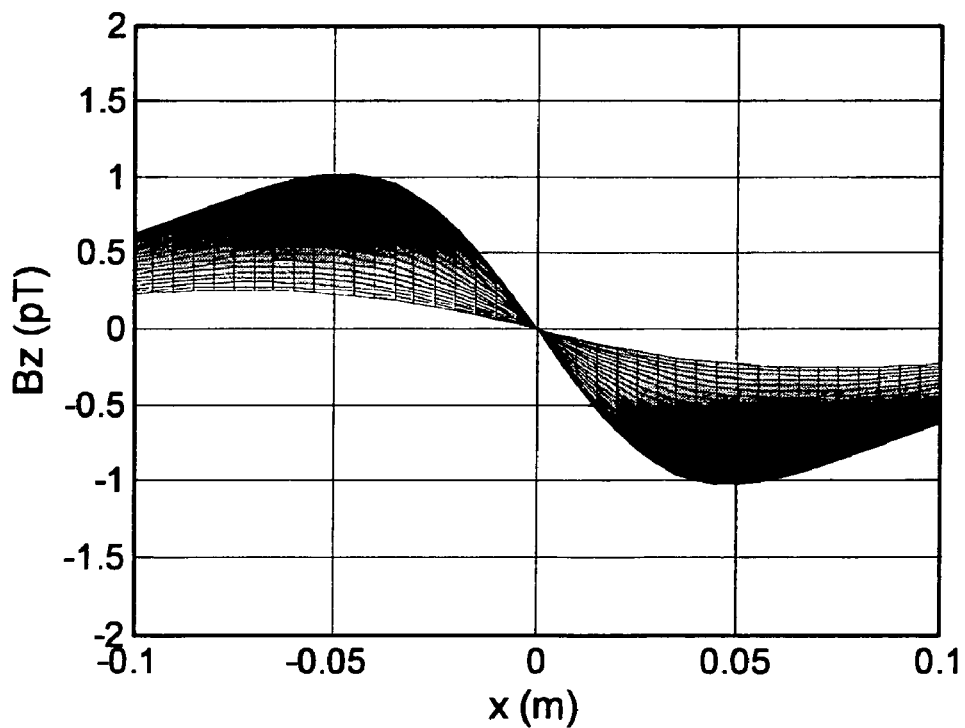
FIG. 4B is a graph showing a projection of FIG. 4A on an x-$B_z$ plane.

A description is given of a signal strength detected by a first-order differential magnetic detection coil with reference to FIG. 4A and FIG. 4B along with FIG. 18B.

FIG. 4A is a graph showing simulation results for a distribution of signal strength detected by a first-order differential magnetic detection coil shown in FIG. 18B. FIG. 4B is a graph showing a projection of FIG. 4A on an x-$B_z$ plane.

In FIGS. 4A and 4B, a current dipole of a cardiac muscle of a typical thirty-week unborn child is assumed as a magnetic signal source in a simulation and a central position of the coil $182a$ of the first-order differential magnetic detection coil 182 is set equal to $(x, y, 0)$ (m), similarly with FIGS. 3A and 3B.

It is known from FIG. 4B that a maximum signal strength detected by the first-order differential magnetic detection coil 182 is substantially equal to 1 pT.

Figure 5A:
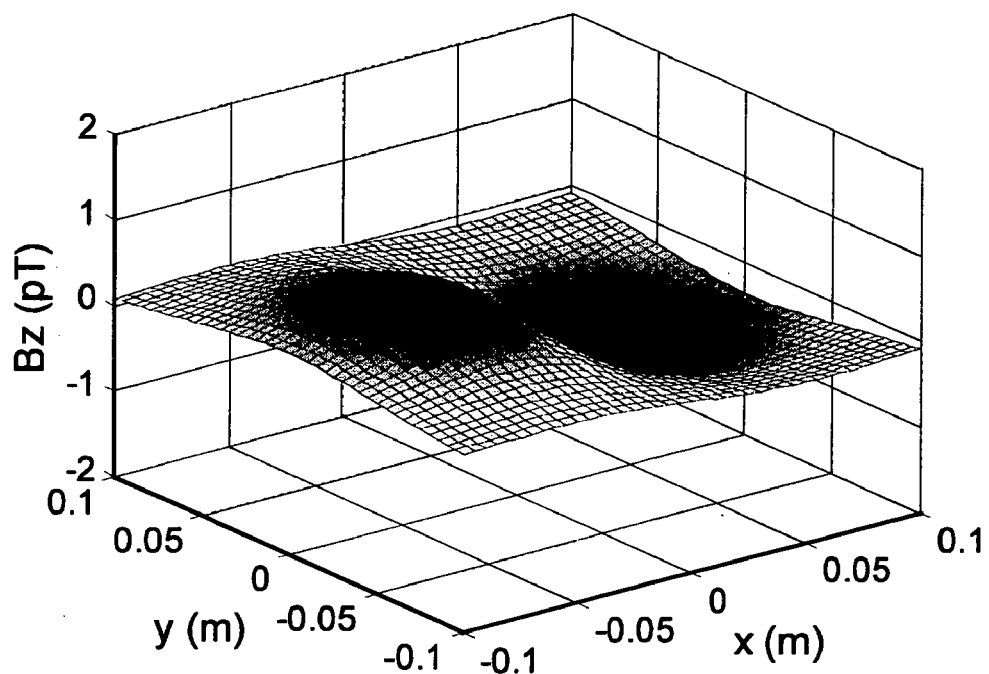
FIG. 5A is a graph showing simulation results for a distribution of signal strength detected by a second-order differential magnetic detection coil shown in FIG. 18C.
Figure 5B:
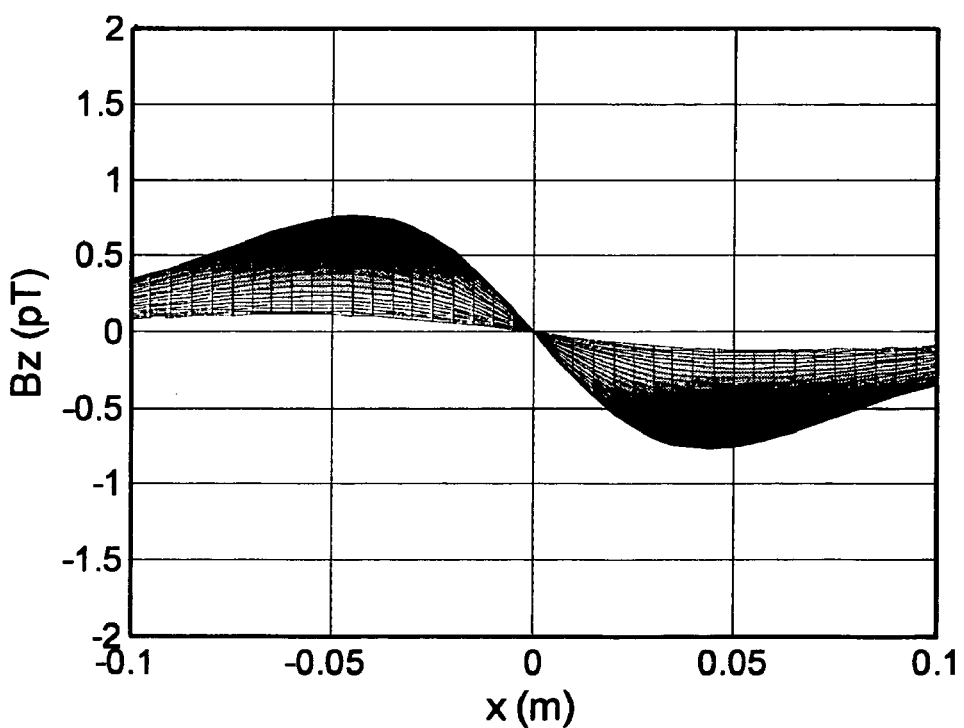
FIG. 5B is a graph showing a projection of FIG. 5A on an x-$B_z$ plane.

Description is given of a signal strength detected by a second-order differential magnetic detection coil with reference to FIG. 5A and FIG. 5B along with FIG. 18C.

FIG. 5A is a graph showing simulation results for a distribution of signal strength detected by a second-order differential magnetic detection coil shown in FIG. 18C. FIG. 5B is a graph showing a projection of FIG. 5A on an x-$B_z$ plane.

Similarly with FIG. 3A and FIG. 3B, a current dipole of a cardiac muscle of a typical thirty-week unborn child is assumed as a magnetic signal source in a simulation and a central position of the coil 183a of the second-order differential magnetic detection coil 183 is set equal to (x, y, 0) (m). It is known from FIG. 5B that a maximum signal strength detected by the second-order differential magnetic detection coil 183 is substantially equal to 0.75 pT.

According to FIG. 3B, FIG. 4B and FIG. 5B, it is known that the signal strength detected by the first-order differential magnetic detection coil 182 is lower than the zero-order differential magnetic detection coil 181, and the signal strength detected by the second-order differential magnetic detection coil 183 is lower than the first-order differential magnetic detection coil 182.

Figure 6A:
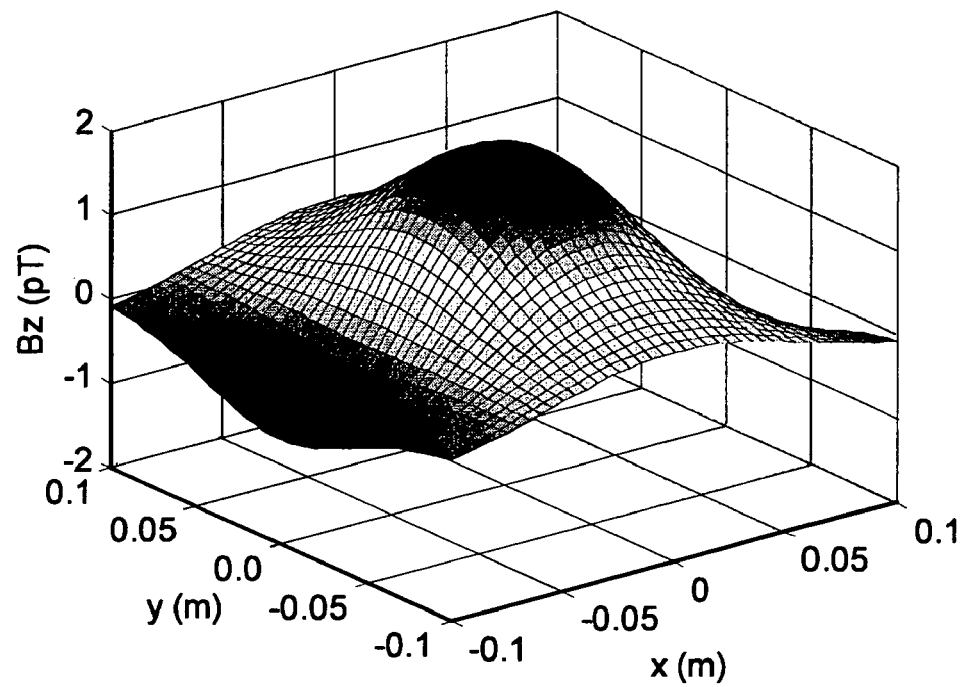
FIG. 6A is a graph showing simulation results for a distribution of signal strength detected by a magnetic detection coil shown in FIG. 1.
Figure 6B:
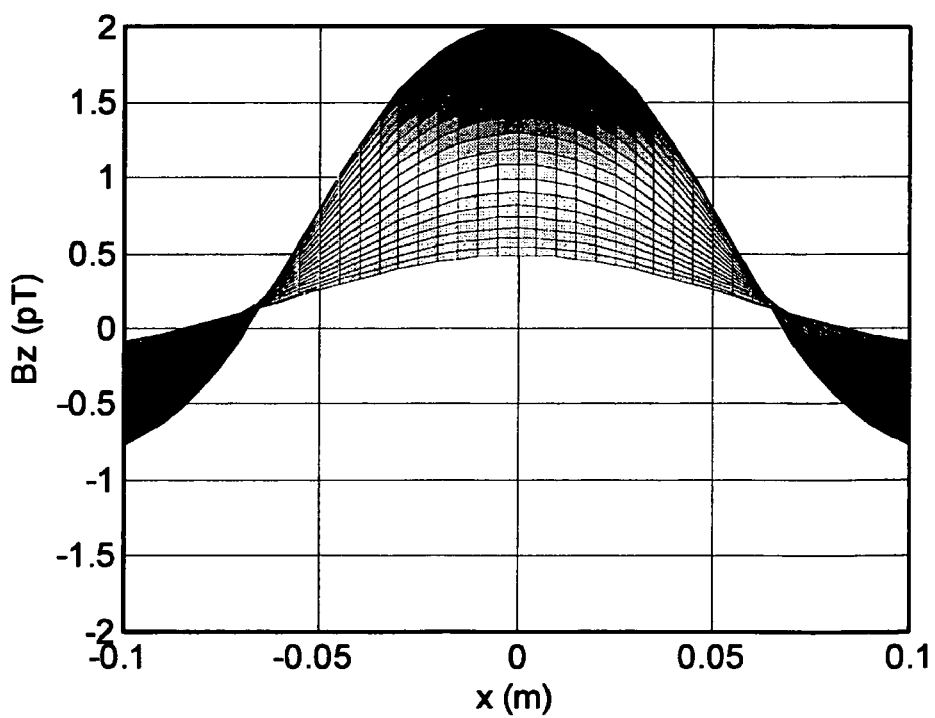
FIG. 6B is a graph showing a projection of FIG. 6A on an x-$B_z$ plane.

A description is given of a signal strength detected by a magnetic detection coil 1 shown in FIG. 1 with reference to FIG. 6A and FIG. 6B.

FIG. 6A is a graph showing simulation results for a distribution of signal strength detected by a magnetic detection coil 1 shown in FIG. 1. FIG. 6B is a graph showing a projection of FIG. 6A on an x-$B_z$ plane.

The center-to-center distance d=$\sqrt{2z_0}$ (see equation (13)) between centers $P_{1a}$ and $P_{1c}$ of the coils 1a and 1c is set substantially equal to 113 (mm) so that an output of the magnetic detection coil 1 according to this embodiment becomes maximal. Also, a middle point of a line connecting the points $P_{1a}$ and $P_{1c}$ is set equal to (x, y, 0) (m). It is observed that the signal strength detected by the magnetic detection coil 1 takes a maximum value at x=0 and y=0, right above the dipole Q. The maximum value obtained from FIG. 6B is substantially equal to 2 pT.

Figure 7A:
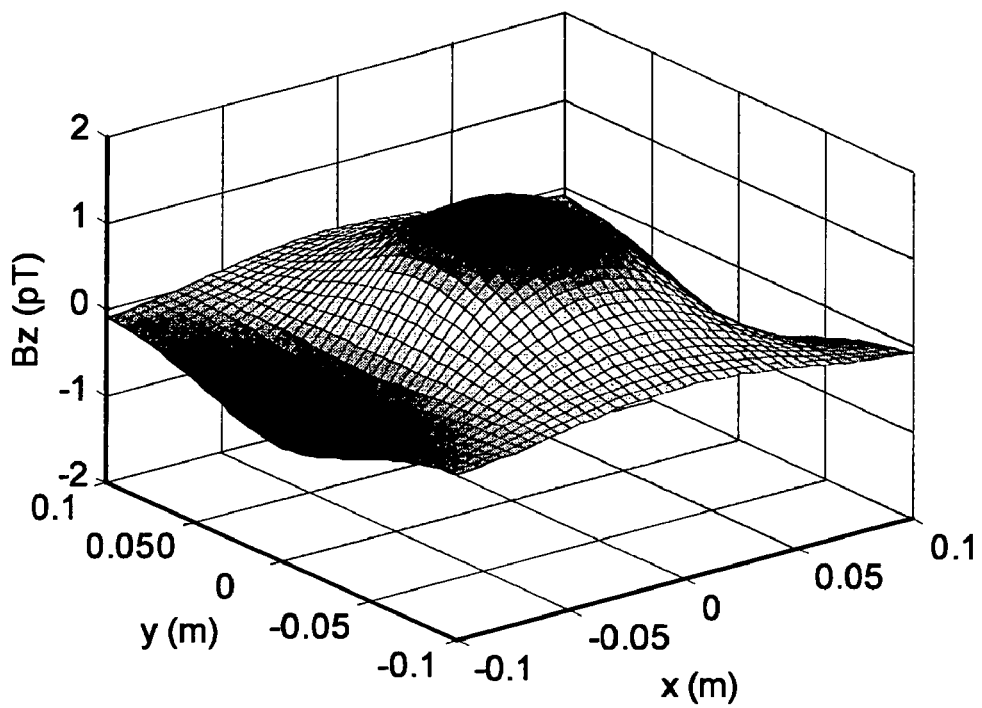
FIG. 7A is a graph showing simulation results for a distribution of signal strength detected by a magnetic detection coil shown in FIG. 2.
Figure 7B:
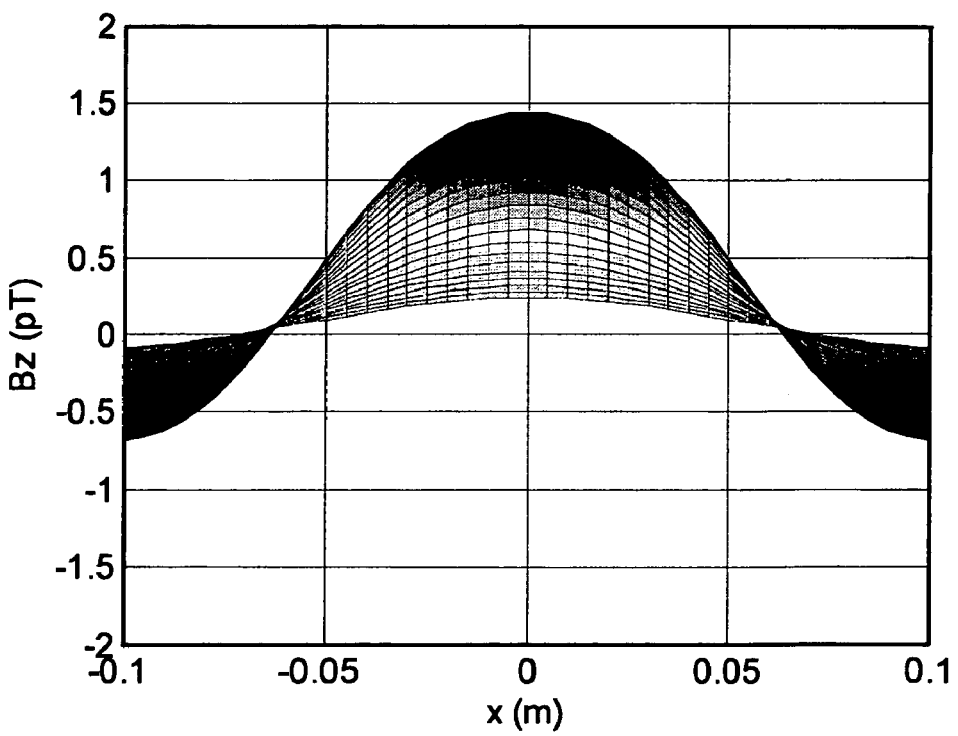
FIG. 7B is a graph showing a projection of FIG. 7A on an x-$B_z$ plane.

A description is given of a signal strength detected by a magnetic detection coil 2 shown in FIG. 2 with reference to FIG. 7A and FIG. 7B.

FIG. 7A is a graph showing simulation results for a distribution of signal strength detected by a magnetic detection coil shown in FIG. 2. FIG. 7B is a graph showing a projection of FIG. 7A on an x-$B_z$ plane.

The center-to-center distance d=$\sqrt{2z_0}$ (see equation (13)) between centers $P_{2a}$ and $P_{2d}$ of the coils 2a and 2d is set substantially equal to 113 (mm) so that an output of the magnetic detection coil 2 becomes maximal. Also, a middle point of a line connecting the points $P_{2a}$ and $P_{2d}$ is set equal to (x, y, 0) (m). It is observed that the signal strength detected by the magnetic detection coil 2 takes a maximum value at x=0 and y=0, right above the dipole Q. The maximum value obtained from FIG. 7B is substantially equal to 1.5 pT.

As described above, the magnetic detection coil 1 shown in FIG. 1 is able to detect a magnetic signal twice as large as that detected by the first-order differential magnetic detection coil 182 shown in FIG. 18B.

Because the magnetic detection coil 1 is expected to decrease an effect of environmental magnetic fields more efficiently than the first-order differential magnetic detection coil 182, it is understood that the magnetic detection coil 1 is able to provide a higher S/N ratio than the first-order differential magnetic detection coil 182.

Figure 9:
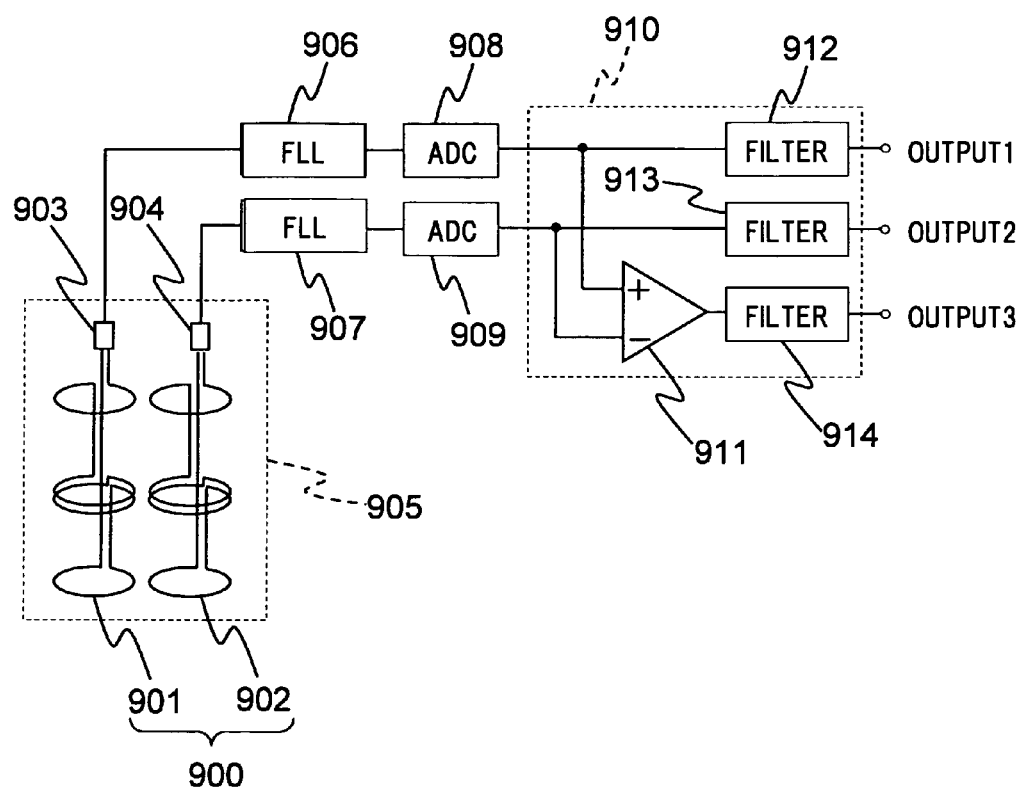
FIG. 9 is a schematic diagram illustrating an apparatus for measurement of a magnetic field used for an experiment of a magnetic detection coil according to an embodiment of the present invention.
Figure 10:
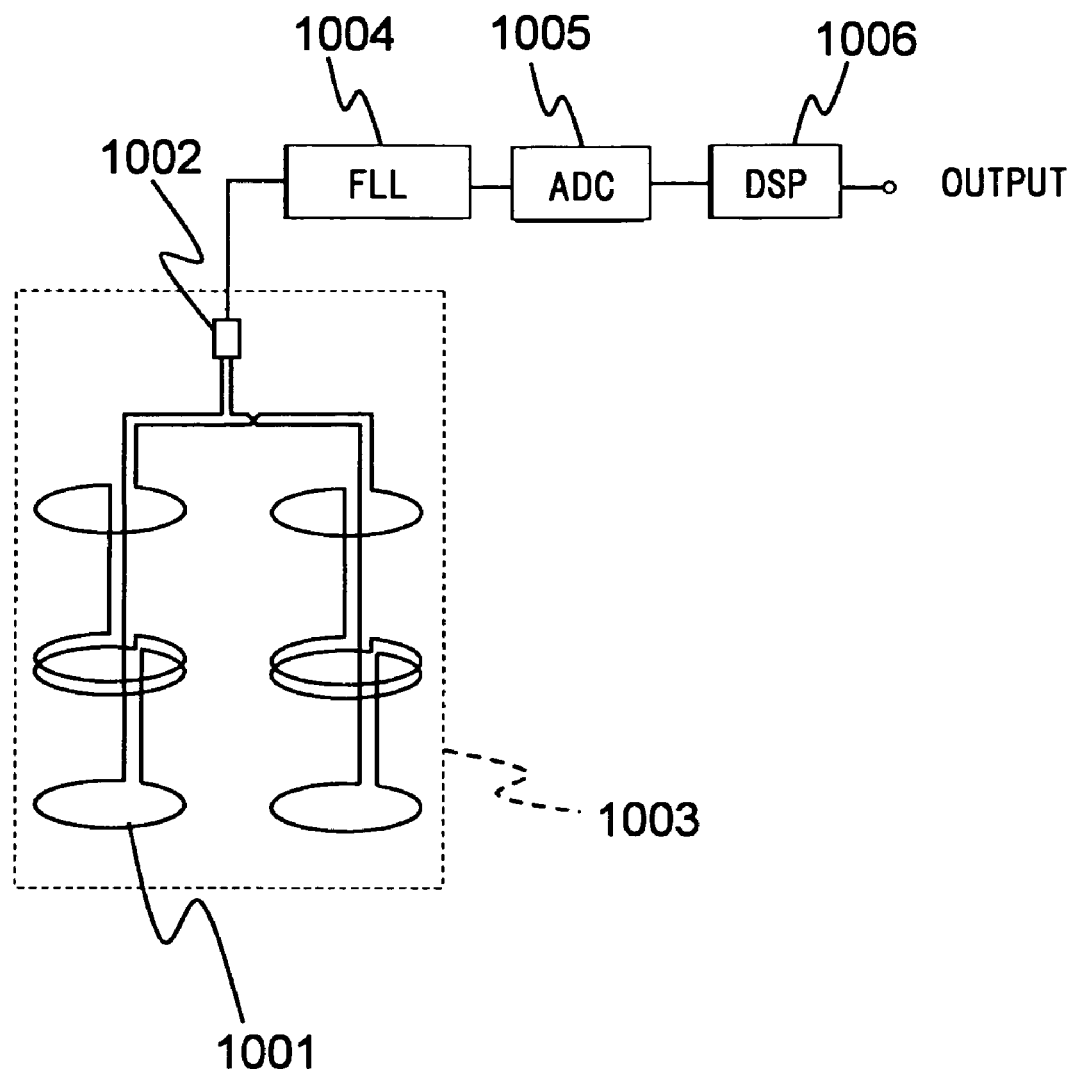
FIG. 10 is a schematic diagram illustrating an apparatus for measurement of a magnetic field according to an embodiment of the present invention.

A magnetic detection coil 1 or 2 is practically applied to an FLL circuit as a magnetic detection coil, as shown in FIGS. 9 and 10.

Figure 8:
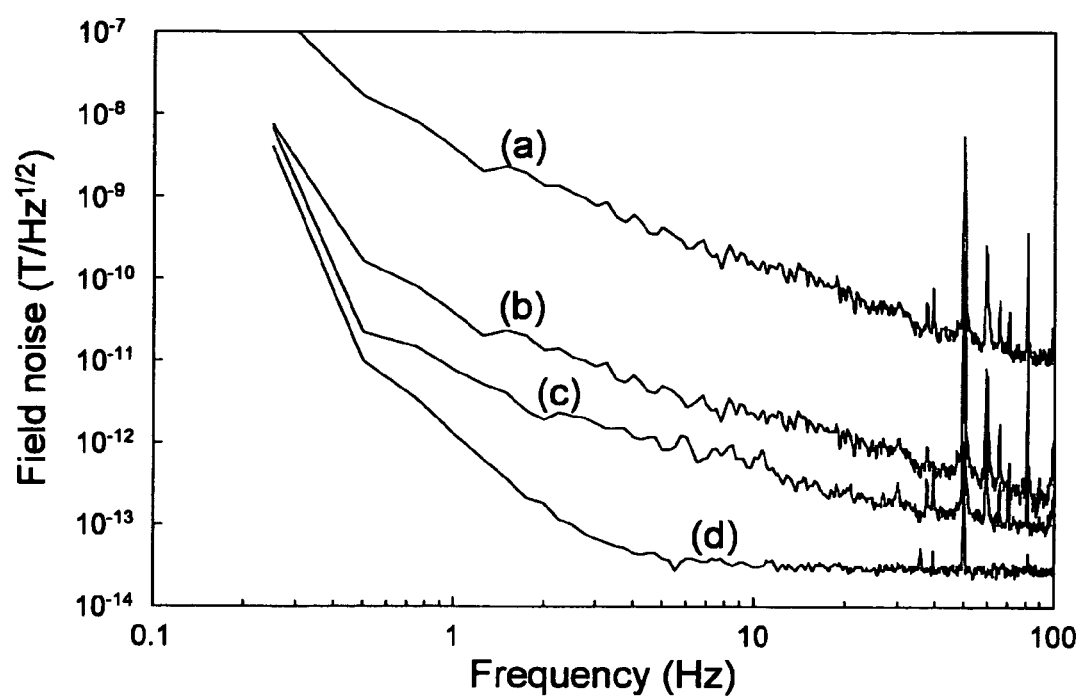
FIG. 8 is a graph showing experimental results which demonstrate advantages provided by a magnetic detection coil according to an embodiment of the present invention.
Figures 18D, 18E:
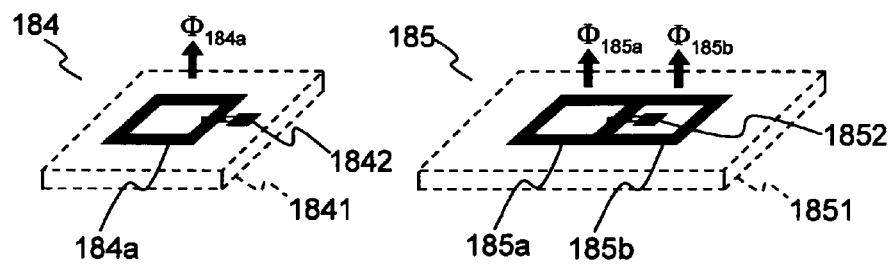
FIG. 18D shows a zero-order differential magnetic detection coil formed on a thin film substrate.
FIG. 18E shows a first-order differential magnetic detection coil formed on a thin film substrate.

A description is given of advantages of the magnetic detection coil according to this embodiment with reference to FIG. 8 along with FIGS. 2 and 18.

FIG. 8 is a graph showing experimental results which demonstrate advantages given by the magnetic detection coil according to this embodiment.

In FIG. 8, a vertical axis represents strength (T/Hz$^{1/2}$) of field noise detected by a magnetic detection coil and a horizontal axis a frequency (Hz) of the field noise.

A curve (a) in FIG. 8 represents a frequency characteristic of output from a fluxgate magnetometer outside a magnetic shield, namely a frequency characteristic of environmental magnetic fields. A curve (b) in FIG. 8 represents a frequency characteristic of output from a second-order differential magnetic detection coil 183 of FIG. 18C outside a magnetic shield. Diameters of coils 183a, 183b and 183c of the second-order differential magnetic detection coil 183 were set equal to 18 mm, respectively. A vertical distance between the two neighboring coils was set equal to 50 mm. A curve (c) in FIG. 8 represents a frequency characteristic of output from a magnetic detection coil 2 shown in FIG. 2 outside a magnetic shield. Diameters of coils 2a to 2f of the magnetic detection coil 2 used for an experiment were set equal to 18 mm, respectively. A vertical distance between the two neighboring coils was set equal to 50 mm. In addition, a center-to-center distance between bobbins 21a and 21b was set equal to 25$\sqrt{2}$ mm. A curve (d) in FIG. 8 represents a frequency characteristic of output from a second-order differential magnetic detection coil 183 inside a magnetic shield, which is the same as the magnetic detection coil used for calculating the curve (b) of FIG. 8.

A reduction rate Sp (dB) is defined by an equation (14), where a magnetic flux density calculated from an output of a magnetic detection coil is denoted as $B_p$ and a magnetic flux density of environmental fields as $B_a$. The reduction rate acquired for a frequency band 0.5-49 Hz by the second-order differential magnetic detection coil 183 was 32-40 dB as shown by curve (b) of FIG. 8. On the other hand, the reduction rate acquired by the magnetic detection coil 2 was 41-58 dB as shown by curve (c) of FIG. 8. The reduction rate acquired by the second-order differential magnetic detection coil 183 with a magnetic shield was 54-83 dB as shown by curve (d) of FIG. 8.

$$S_p = 20 \log|B_a/B_p| \quad (14)$$

The reason why reduction rates differ from one another according to frequencies is that a distance between a source of an environmental magnetic field and a magnetic detection coil depends on a frequency. Generally speaking, the more apart from a magnetic detection coil a magnetic field source is located, the less steep magnetic gradient the magnetic field source has. A reduction rate of the magnetic detection coil tends to be higher, accordingly. Introducing a value, which is obtained by integration of field noise over a bandwidth of 0.5-49 Hz, a noise reduction rate of 40 dB was calculated for the second-order differential magnetic detection coil 183 as shown by the curve (b) in FIG. 8. This value corresponds to a magnetic signal value, which results from an output of a magnetic detection coil filtered by a bandpass filter having a passing band of 0.5-49 Hz. In contrast, a noise reduction rate of the magnetic detection coil 2 was 54 dB as shown by curve (c) of FIG. 8. Also, a noise reduction rate for a combination of a magnetic shield and the second-order differential magnetic detection coil 183 was 73 dB as shown by curve (d) of FIG. 8. The results described above lead to an observation that the noise reduction rate of the magnetic detection coil 2 is higher by 14 dB than that of the second-order differential magnetic detection coil 183.

Description is given of advantages given by a magnetic detection coil 2 shown in FIG. 2 with reference to FIGS. 9 to 11 along with FIGS. 2 and 18.

FIG. 9 is a schematic diagram illustrating an apparatus for measurement of a magnetic field, which is used for an experiment demonstrating advantages provided by the magnetic detection coil according to this embodiment.

The objective of this experiment is to compare wave shapes of magnetic signals detected by magnetic detection coils in magnetocardiography, which is carried out for adults using a second-order differential magnetic detection coil 183 and a magnetic detection coil 900 of this embodiment without a magnetic shield.

Figure 17:
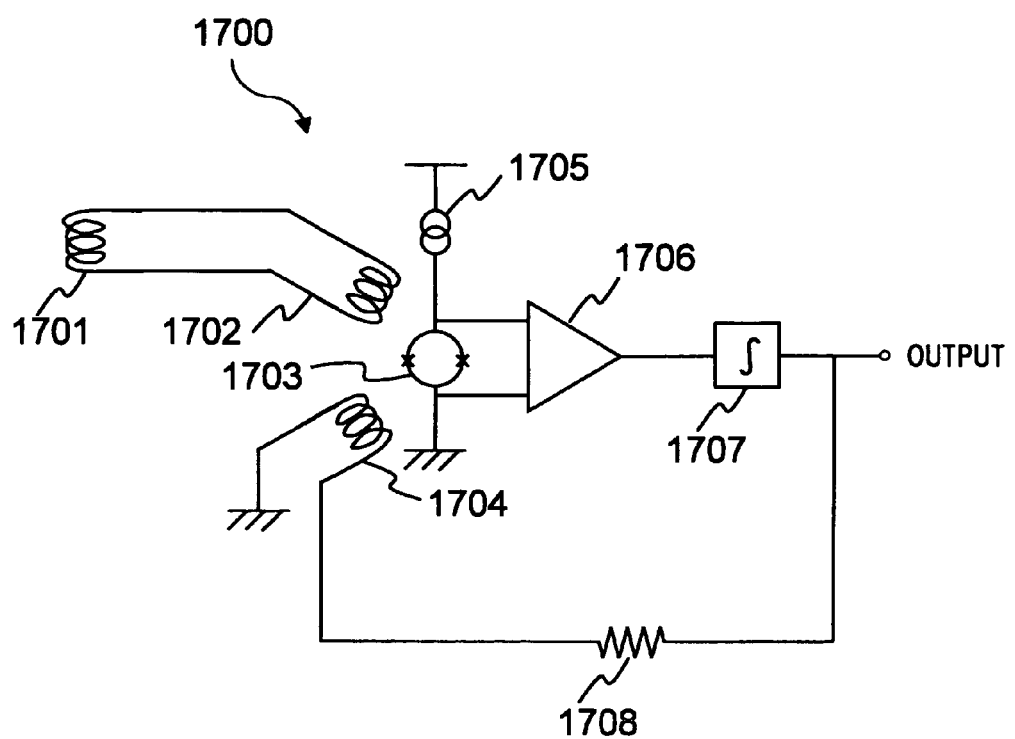
FIG. 17 is a schematic diagram illustrating architecture of a Flux Locked Loop (FLL) circuit in a typical apparatus for measurement of a magnetic field.

Magnetic fluxes detected by two pieces of second-order differential magnetic detection coils 901 and 902 are transmitted to SQUID substrates 903 and 904, respectively. It should be noted that each of the SQUID substrates 903 and 904 includes an input coil 1702, a SQUID 1703 and a feedback coil 1704 shown in FIG. 17. The second-order differential magnetic detection coils 901 and 902 each have a diameter 18 mm and a vertical distance 50 mm between neighboring coil loops. A center-to-center distance between the second-order differential magnetic detection coils 901 and 902 is set equal to 25√2 mm. This means that two pieces of second-order differential magnetic detection coils are arranged in parallel. The second-order differential magnetic detection coils 901 and 902 and the SQUID substrate 903 and 904 are cooled in a cryostat 905. Liquid helium is charged in the cryostat 905, which is thermally insulated by a vacuum insulation layer. The SQUID substrates 903 and 904 are controlled by FLL circuits 906 and 907, respectively. An output from the FLL circuit 906 and an output from the FLL circuit 907, which are transformed by analogue to digital (AD) converters 908 and 909, respectively, are sent to a digital signal processor (DSP) 910, where the output undergoes real-time digital signal processing. In digital signal processing conducted by the DSP 910, a differential element 911 generates a difference between two input signals. Filters 912, 913 and 914 each include a notch filter for eliminating noise in frequencies of a commercial power supply and a bandpass filter having a passing band of 1-50 Hz. In this connection, output 1 and output 2 are magnetic signals, which are detected by the second-order differential magnetic detection coils 901 and 902 respectively, and subjected to a filtering process. Output 3 is a differential signal between the magnetic signals detected by the second-order differential magnetic detection coils 901 and 902, and it is subjected to a filtering process. In this way, the output 3 in FIG. 9 corresponds to the magnetic signal detected by the magnetic detection coil 2 in FIG. 2 which is subjected to a filtering process.

FIG. 10 is a schematic diagram illustrating an apparatus for measurement of a magnetic field according to an embodiment.

Magnetic fluxes detected by a magnetic detection coil 1001 having the similar architecture to the magnetic detection coil 2 shown in FIG. 2 is transmitted to a SQUID substrate 1002. The SQUID substrate 1002 includes an input coil 1702, a SQUID 1703 and a feedback coil 1704 shown in FIG. 17. The magnetic detection coil 1001 and the SQUID substrate 1002 are cooled in a cryostat 1003. Liquid helium is charged in the cryostat 1003, which is thermally insulated by a vacuum insulation layer. The SQUID substrate 1002 is controlled by an FLL circuit 1004. An output from the FLL circuit 1004, which is transformed by an AD converter 1005, is sent to a DSP 1006, where the output undergoes real-time digital signal processing. Magnetic fluxes detected by the magnetic detection coil 1001 correspond to a difference between fluxes detected by the second-order differential magnetic detection coils 901 and 902 shown in FIG. 9. It is known from the simulation results shown in FIGS. 4 to 6 described above that the magnetic detection coil 1001 is able to detect larger magnetic signals than the second-order differential magnetic detection coils 901 and 902. The magnetic coil 1001 is able not only to decrease noise more but also to detect larger magnetic signals than the second-order differential magnetic detection coils 901 and 902. In this way, the magnetic detection coil 1001 is able to provide a higher S/N ratio for detection of magnetic signals compared with the second-order differential magnetic detection coils 901 and 902.

It should be noted that the apparatus for measurement of a magnetic field shown in FIGS. 9 and 10 can be applied to practical use shown in FIGS. 14 to 16 to be described later.

Figure 11A:
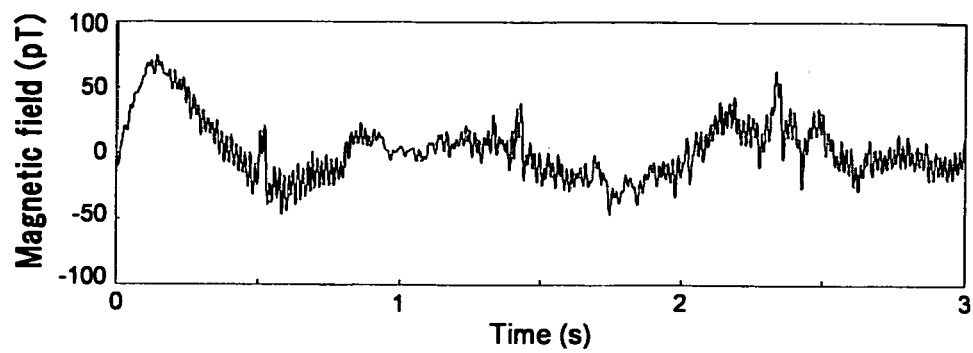
FIG. 11A, FIG. 11B and FIG. 11C are graphs showing histories of output 1, output 2 and output 3 shown in FIG. 9, respectively.
Figure 11B:
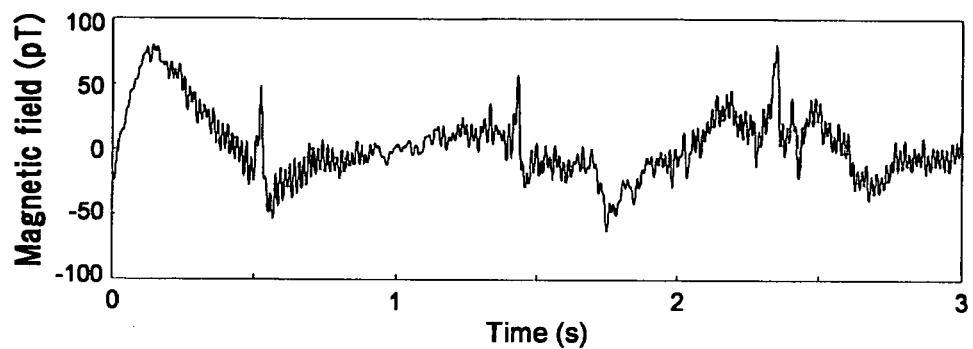
Figure 11C:
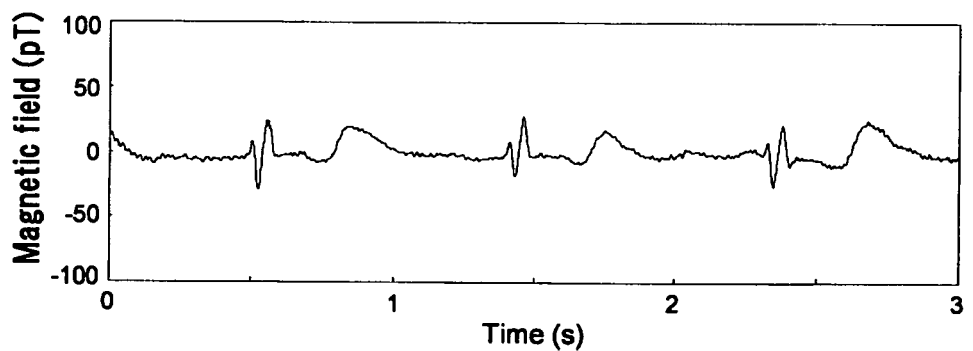

FIG. 11A to FIG. 11C are graphs showing results of magnetocardiography conducted for an adult by an apparatus for measurement of a magnetic field shown in FIG. 9. In each graph, a vertical axis represents magnetic flux density (pT) and a horizontal axis represents time (sec).

FIG. 11A, FIG. 11B and FIG. 11C are graphs showing histories of the output 1, the output 2 and the output 3 shown in FIG. 9, respectively.

Although a peak of QRS wave is observable in cardiomagnetic wave shapes shown in FIG. 11A and FIG. 11B, noise of about some tens of hertz and fluctuations with respect to a baseline curve are prominently observed. This is due to the fact that an effect of environmental magnetic fields is not sufficiently decreased. In contrast, cardiomagnetic wave shapes are clearly detected in FIG. 11C. The noise of some tens of hertz and the fluctuations with respect to the baseline curve, which appear in FIGS. 11A and 11B, are decreased by differentiation of in plane direction of the magnetic detection coil. In this way, T waves in addition to QRS waves are clearly observed. The experimental results described above demonstrate that the magnetic detection coil 2 of FIG. 2 possesses a higher S/N ratio than the second-order differential magnetic detection coil 183 of FIG. 18C and it is able to obtain clear cardiomagnetic wave shapes even if measurement is conducted without a magnetic shield.

Because an effect due to environmental magnetic fields is decreased more for magnetic signals (output 3 of FIG. 9) than for those (output 1 and output 2 of FIG. 9) obtained by the individual second-order differential magnetic detection coils 901 and 902, the magnetic detection coil 900 is able to transmit magnetic signals with reduced field noise.

Wave shapes obtained from output of the apparatus for measurement of a magnetic field shown in FIG. 10 are substantially the same as those obtained from the output 3 of the apparatus for measurement of a magnetic field shown in FIG. 9. Because the apparatus for measurement of a magnetic field shown in FIG. 10 reduces the number of components such as a SQUID, an FLL circuit and an AD converter as well as signal processing to half compared with its counterpart shown in FIG. 9, it is possible to obtain signals with high S/N ratios at a lower cost.

In FIG. 9, it may be possible to alternatively adopt a first-order differential magnetic detection coil in place of the second-order differential magnetic detection coil. In FIG. 10, it may also be possible to alternatively adopt a magnetic detection coil 1 of FIG. 1 in place of a magnetic detection coil 2 of FIG. 2.

d. Arrangement of Magnetic Detection Coils

Figure 12:
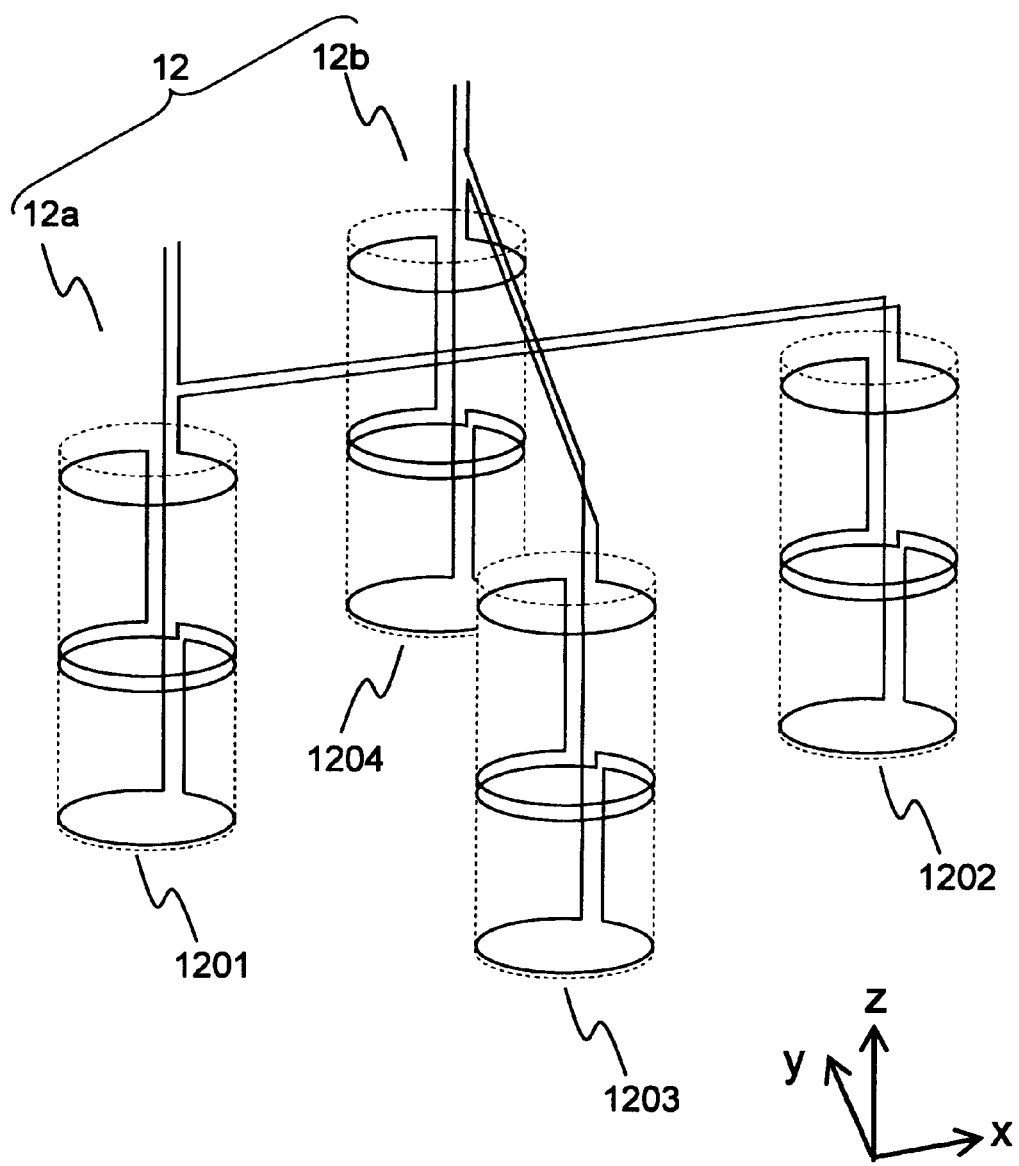
FIG. 12 is a perspective view showing an arrangement of magnetic detection coils according to an embodiment of the present invention.

A description is given of an example for arrangement of magnetic detection coils according to an embodiment with reference to FIG. 12 and FIG. 13 along with FIG. 2.

FIG. 12 is a perspective view showing an arrangement of magnetic detection coils according to this embodiment.

Magnetic detection coils 12a and 12b each have the similar architecture as a magnetic detection coil 2 shown in FIG. 2. In other words, the magnetic detection coils 12a and 12b each have a pair of differential magnetic detection coils. The magnetic detection coil 12a includes a coil 1201 of second-order differential type and a coil 1202 of the same type having a winding direction opposite to the coil 1201. Similarly, the magnetic detection coil 12b includes a coil 1203 of second-order differential type similar to the architecture of FIG. 18C and a coil 1204 of the same type having a winding direction opposite to the coil 1201. A pair of the magnetic detection coils 12a and 12b is referred to as a magnetic detection coil pair 12. It should be noted that the magnetic detection coils 12a and 12b are arranged so that their directions of first-order differential in a horizontal direction are perpendicular to each other.

Figure 13A:
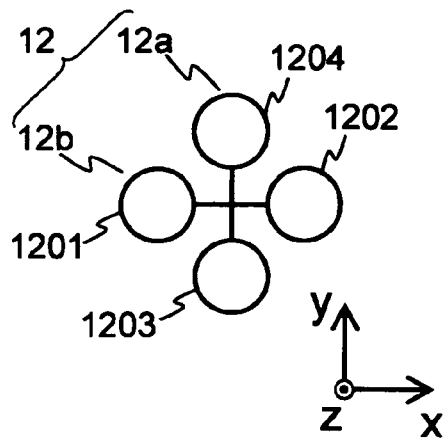
FIG. 13A is a top view schematically illustrating a magnetic detection coil pair shown in FIG. 12.
Figure 13B:
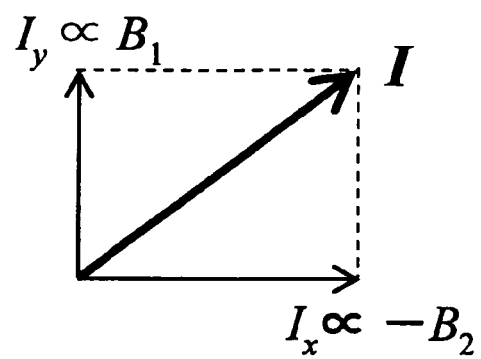
FIG. 13B illustrates relationship among a current vector of a magnetic field source and magnetic flux densities in a z-direction.
Figure 13C:
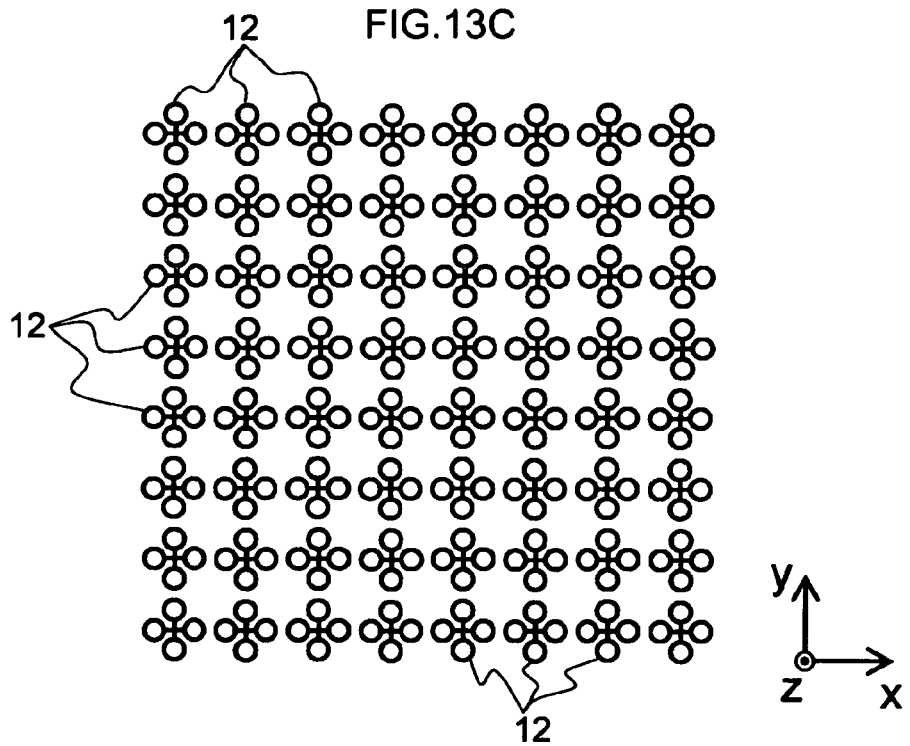
FIG. 13C is a schematic diagram illustrating an arrangement of 64 magnetic detection coil pairs, each pair the same as that shown in FIG. 12, in a form of 8 by 8 lattices.

FIG. 13A is a top view schematically illustrating a magnetic detection coil pair of FIG. 12. FIG. 13B illustrates a relationship among a current vector I of a magnetic field source and magnetic flux densities $B_1$ and $B_2$ in a z-direction. The magnetic flux density $B_1$ detected by the magnetic detection coil 12a is differentiated in an x-axis direction. The magnetic flux density $B_2$ detected by the magnetic detection coil 12b is differentiated in a y-axis direction. FIG. 13C is a schematic diagram illustrating an arrangement of 64 magnetic detection coil pairs, each pair the same as that shown in FIG. 12, in a form of 8 by 8 lattices.

Generally speaking, when current such as a cardio muscle current flows in an x-axis direction, a magnetic field generated by the current is obtained through magnetic signals detected by a magnetic detection coil, which is differentiated in a y-axis direction. If a magnetic detection coil differentiated in an x-axis direction is used on the other hand, almost no signals are detected. This means that when a magnetic detection coil horizontally differentiated is used, it is preferable to select a magnetic detection coil which is differentiated in a direction perpendicular to that of a current of a magnetic field source. Because a direction of current to be measured, such as a cardio muscle current, is not known in advance, it is preferable to arrange two pieces of magnetic detection coils 2 according to this embodiment so that they perpendicularly intersect each other, similarly with the magnetic detection coil pair 12 shown in FIG. 12.

It is possible to calculate a vector sum of the magnetic flux density $B_1$ detected by the magnetic detection coil 12a and the magnetic flux density $B_2$ detected by the magnetic detection coil 12b by an equation (15).

$$B_0 = \sqrt{B_1^2 + B_2^2} \qquad (15)$$

The equation (15) enables reliable detection of a magnetic field generated by a current source irrespective of a direction of the current source to be measured.

When a current vector of a magnetic field source is denoted as $I=(I_x, I_y)$, an x-component $I_x$ and a y-component $I_y$ of the current are approximated by an equation (16) using changes $\Delta B_z/\Delta x$ and $\Delta B_z/\Delta y$ in magnetic flux densities. $\Delta B_z/\Delta x$ is a change in a magnetic flux density in a z-axis direction, which is first-order differentiated in an x-axis direction. $\Delta B_z/\Delta y$ is a change in a magnetic flux density in a z-axis direction, which is first-order differentiated in a y-axis direction (see H. Hosaka and D. Cohen, "Visual determination of generators of the magnetocardiogram" Journal of Electrocardiology USA, 1976, Volume 9, pp. 426-432).

$$(I_x, I_y) \propto (-\Delta B_z/\Delta y, \Delta B_z/\Delta x) \qquad (16)$$

An x-component $I_x$ and y-component $I_y$ of the current of a magnetic field source are approximated by an equation (17) using the magnetic flux density $B_1$ differentiated in an x-axis direction detected by the magnetic detection coil 12a and the magnetic flux density $B_2$ differentiated in a y-axis direction detected by the magnetic detection coil 12b.

$$(I_x, I_y) \propto (-B_2, B_1) \qquad (17)$$

In this way, the magnetic detection coil pair 12 is able to detect the current of the magnetic field source approximately as a current vector.

As shown in FIG. 13B, the current can be represented as a vector by the magnetic flux densities $B_1$ and $B_2$ detected by the magnetic detection coils 12a and 12b, respectively.

As described above, it is possible to detect a distribution of a magnetic field by arranging a plurality of magnetic detection coil pairs 12. In addition, the equation (17) allows detection of a distribution of current vectors of a magnetic field source (current vector field). In this way, it is possible to estimate a location where a current of cardio muscle flows without worrying about a direction of the current for magnetocardiography. It is also possible to estimate a location where a neural current flows without worrying about a direction of the current for magnetoencephalography.

An apparatus 1400 for measurement of a magnetic field with magnetic detection coils according to an embodiment is now described with reference to FIG. 14 as well as FIGS. 1 and 2.

Figure 14:
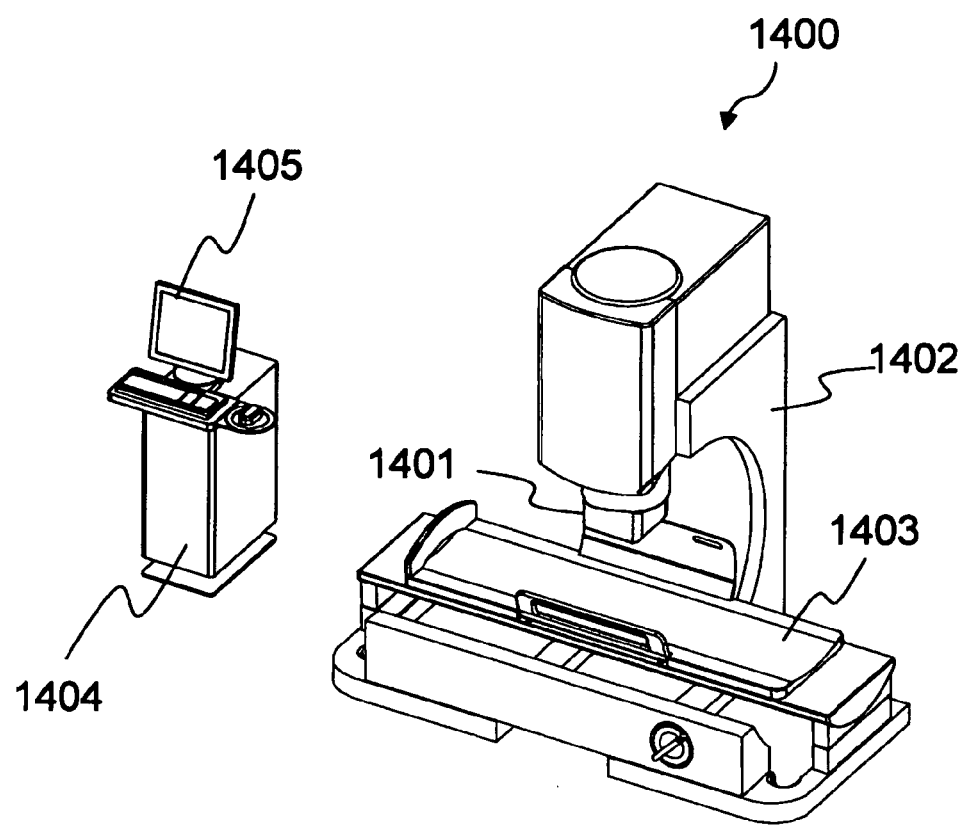
FIG. 14 is a perspective view illustrating overall architecture for an apparatus for measurement of a magnetic field according to an embodiment of the present invention.

FIG. 14 is a perspective view illustrating overall architecture for the apparatus for measurement of a magnetic field according to this embodiment.

In the apparatus 1400, magnetic detection coils 1 shown in FIG. 1 or magnetic detection coils shown in FIG. 2 and a SQUID are kept in low temperatures inside a cryostat 1401. With regard to arrangement of the magnetic detection coils, pairs of magnetic detection coils, each pair having two magnetic detection coils as shown in FIG. 12, are arranged in a configuration shown in FIG. 13. It should be noted that each magnetic detection coil is so arranged that a plane of a coil loop of a magnetic detection coil is parallel with a bottom plane of the cryostat 1401. Liquid helium is charged in the cryostat 1401, which is thermally insulated by a vacuum insulation layer. The cryostat 1401 is supported by a gantry 1402. A testee for measurement of biomagnetism lies on a bed 1403, and a height and horizontal position of the bed 1403 are adjusted so that a measurement area (a chest or back in case of magnetocardiography, for example) is positioned near the bottom plane of the cryostat 1401. A measurement and control circuit 1404 controls a SQUID magnetometer to transform detected magnetic signals into voltage signals, which are transmitted to a signal process and display device 1405. The device 1405 is able to eliminate an effect of environmental magnetic fields by a DSP so as to obtain magnetic signals generated by an organism of the testee and to display in real time a wave shape of magnetocardiography or magnetoencephalography, a diagram showing isomagnetic lines, a diagram showing current distribution and the like.

e. Example for Application of Magnetic Detection Coils: Apparatus for Magnetocardiography of Unborn Child A description is given of an apparatus 1500 for magnetocardiography of an unborn child with reference to FIG. 15 along with FIGS. 1 and 2.

Figure 15:
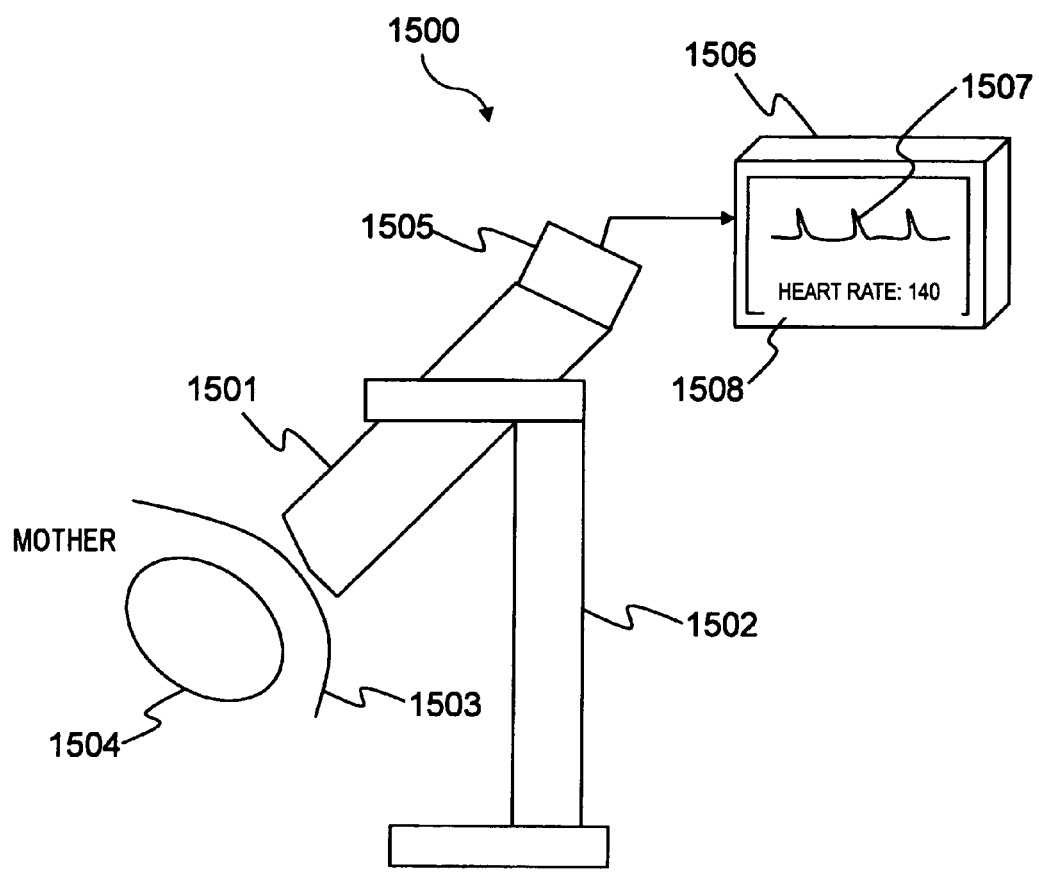
FIG. 15 is a perspective view illustrating an apparatus for magnetocardiography of an unborn child according to an embodiment of the present invention.

FIG. 15 is a perspective view illustrating the apparatus for magnetocardiography of an unborn child according to an embodiment.

In the apparatus 1500, magnetic detection coils 1 shown in FIG. 1 or magnetic detection coils shown in FIG. 2 and a SQUID are kept in low temperatures inside a cryostat 1501. With regard to arrangement of the magnetic detection coils, pairs of magnetic detection coils, each pair having two magnetic detection coils as shown in FIG. 12, are arranged in a configuration shown in FIG. 13. It should be noted that each magnetic detection coil is so arranged that a plane of a coil loop of a magnetic detection coil is in parallel with a bottom plane of the cryostat 1501. Liquid helium is charged in the cryostat 1501, which is thermally insulated by a vacuum insulation layer. The cryostat 1501 is supported by a gantry 1502. The cryostat 1501 is not only movable in horizontal and vertical directions, but also adjustable in diagonal direction. A position of the cryostat 1501 is so adjusted that magnetic detection coils are positioned near an abdominal region of a mother 1503. A measurement and control circuit 1505 controls a SQUID magnetometer to transform detected magnetic signals into voltage signals, which are transmitted to a signal process and display device 1506. The device 1506 eliminates an effect of environmental magnetic fields and cardiomagnetic signals deriving from the mother 1503 by a DSP so as to detect cardiomagnetic signals of an unborn child 1504. The device 1506 displays in real time not only a cardiomagnetic wave shape 1507, but also a heart rate 1508, which is calculated based on the cardiomagnetic signals from the unborn child 1504. The apparatus for magnetocardiography of an unborn child described above is able to monitor in real time the cardiomagnetic wave shape 1507 and the heart rate 1508 of the unborn chilled 1504.

f. Example for Application of Magnetic Detection Coils: Apparatus for Magnetoencephalography Description is given of an apparatus 1600 for magnetoencephalography with reference to FIG. 16 along with FIGS. 1 and 2.

Figure 16:
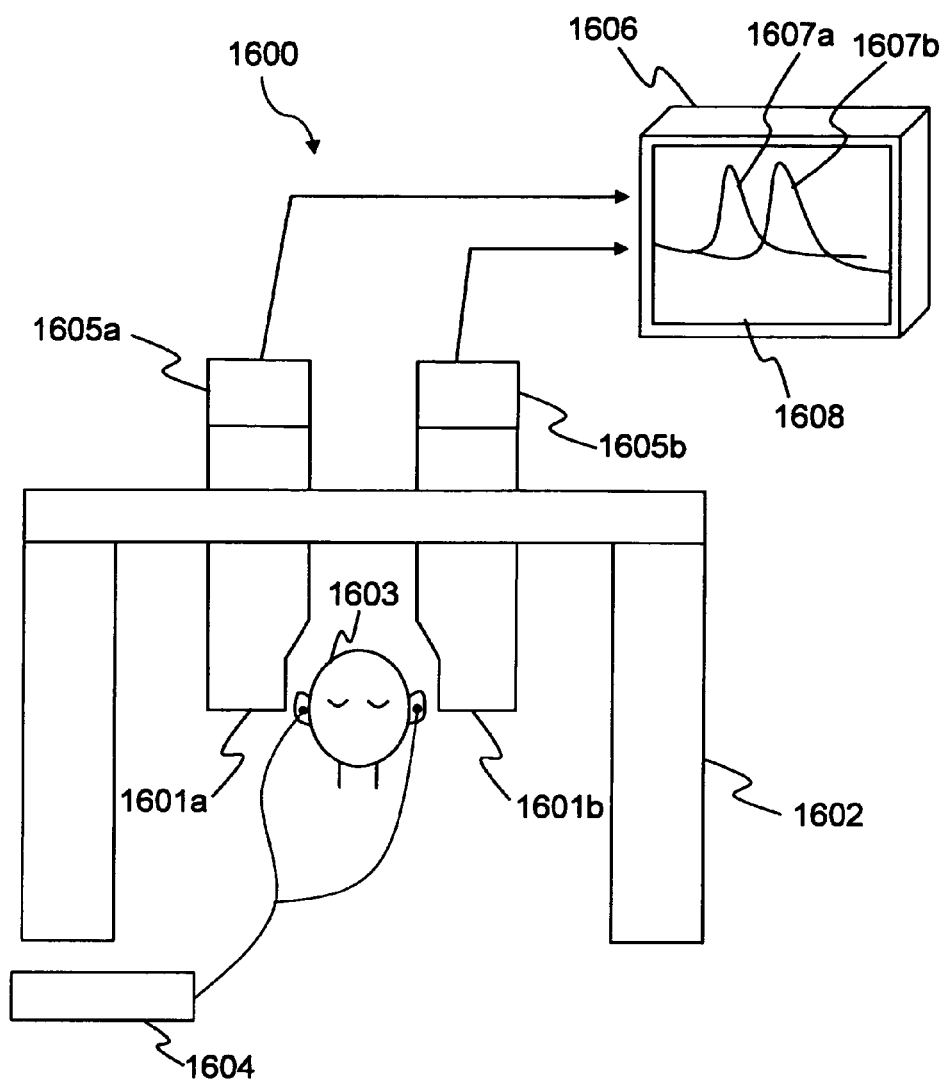
FIG. 16 is a perspective view illustrating an apparatus for magnetoencephalography according to an embodiment.

FIG. 16 is a perspective view illustrating the apparatus for magnetoencephalography according to an embodiment.

In the apparatus 1600, magnetic detection coils 1 shown in FIG. 1 or magnetic detection coils 2 shown in FIG. 2 and SQUID's are kept in low temperatures inside cryostats 1601a and 1601b. With regard to arrangement of the magnetic detection coils, pairs of magnetic detection coils, each pair having two magnetic detection coils as shown in FIG. 12, are arranged in a configuration shown in FIG. 13. It should be noted that each magnetic detection coil is so arranged that a plane of a coil loop of the magnetic detection coil is in parallel with a side surface of the cryostat 1601a or 1601b. Liquid helium is charged in the cryostats 1601a and 1601b, which are thermally insulated by vacuum insulation layers. The cryostats 1601a and 1601b are supported by a gantry 1602. The cryostats 1601a and 1601b are not only movable in horizontal and vertical directions, but also adjustable in diagonal direction. Positions of the cryostats 1601a and 1601b are so adjusted that magnetic detection coils are positioned near a head of a testee 1603. Measurement and control circuits 1605a and 1605b control SQUID magnetometers to transform detected magnetic signals into voltage signals, which are transmitted to a signal process and display device 1606. The device 1606 eliminates an effect of environmental magnetic fields by a DSP so as to detect encephalomagnetic signals of the testee 1603, displaying real-time encephalomagnetic wave shapes 1607a and 1607b. The apparatus 1600 includes a device 1604 for stimulating auditory sense, which is used for giving vocal stimuli to ears of the testee 1603. The signal process and display device 1606 monitors a real-time reaction of the testee 1603. The device 1606 is able to calculate a time difference between peaks of the encephalomagnetic wave shapes 1607a and 1607b, displaying in real time a transmission time 1608. The apparatus 1600 is able to measure a spontaneous brain magnetic field and a phenomenon-related brain magnetic field in addition to a brain magnetic field evoked by a sensory stimulus, which is a response to an auditory stimulus, visual stimulus and somatic sensation stimulus.

A magnetic detection coil, which is a first-order or second-order differential magnetic detection coil, has been described as an example for the embodiment. The magnetic detection coil according to this embodiment detects signals differentiated in two different directions. It may be possible to alternatively select a magnetic detection coil which is third-order or more differentiated in a vertical direction, for example.

In the embodiment described above, magnetocardiography has been picked up as an example. The apparatus for measurement of biomagnetism according to this embodiment can be applied to measurement of a magnetic field generated through neural activities by a brain of a testee and to measurement of a heart magnetic field of an unborn child inside a mother.

In the embodiment described above, a SQUID magnetometer has been selected as an example to transform magnetic fluxes detected by the magnetic detection coils into voltage values. Other than this example, it may be possible to alternatively adopt other magnetometers such as a magnetoresistance element, a giant magnetoresistance element, a fluxgate magnetometer, an optical pumping magnetometer and the like. It may also be possible to alternatively adopt a cryogenic cooler and a SQUID cooled by liquid nitrogen if it is made of high-temperature superconducting material.

This embodiment provides an apparatus for measurement of biomagnetism having a high S/N ratio which is able to carry out more sensitive and accurate measurement of biomagnetism, which allows measurement of biomagnetism under an environment without a magnetic shield.

What is claimed is:

1. A magnetic detection coil, comprising:
   at least two second-order differential coils arranged in parallel, spaced a predetermined distance apart from each other, and composed of at least one of a superconductor or a metal material,
   wherein each of the at least two second-order differential coils comprises at least respective first, second, and third coils arranged in this order,
   wherein the respective first coil and the respective third coil of each second-order differential coil have mutually identical loop directions,
   wherein the respective second coil and the respective first coil of each second-order differential coil have mutually different loop directions,
   wherein the respective second coil and the respective third coil of each second-order differential coil have mutually different loop directions,
   wherein the respective first coil of a first second-order differential coil of the at least two second-order differential coils and the respective second coil of a second second-order differential coil of the at least two second-order differential coils have mutually identical loop directions, and
   wherein the respective second coil of the first second-order differential coil of the at least two second-order differential coils and the respective first coil of the second second-order differential coil of the at least two second-order differential coils have mutually identical loop directions.

2. An apparatus for measurement of a magnetic field, the apparatus comprising:

a magnetic detection coil; and a superconducting quantum interference device to which magnetic signals detected by the magnetic detection coil are transmitted, wherein the magnetic detection coil includes at least two second-order differential coils arranged in parallel, spaced a predetermined distance apart from each other, and composed of at least one of a superconductor or a metal material, wherein each of the at least two second-order differential coils comprises at least respective first, second, and third coils arranged in this order, wherein the respective first coil and the respective third coil of each second-order differential coil have mutually identical loop directions, wherein the respective second coil and the respective first coil of each second-order differential coil have mutually different loop directions, wherein the respective second coil and the respective third coil of each second-order differential coil have mutually different loop directions, wherein the respective first coil of a first second-order differential coil of the at least two second-order differential coils and the respective second coil of a second second-order differential coil of the at least two second-order differential coils have mutually identical loop directions, wherein the respective second coil of the first second-order differential coil of the at least two second-order differential coils and the respective first coil of the second second-order differential coil of the at least two second-order differential coils have mutually identical loop directions, and wherein the magnetic detection coil detects a magnetic flux that is based on a difference between a first magnetic flux penetrating the first second-order differential coil and a second magnetic flux penetrating the second second-order differential coil.

3. The apparatus according to claim 2, further comprising a plurality of magnetic detection coils each of which includes a pair of magnetic detection coils arranged to intersect with each other.

4. The apparatus according to claim 3, wherein each pair of magnetic detection coils intersect perpendicularly with each other.

5. The apparatus according to claim 3, wherein the plurality of magnetic detection coils includes a plurality of pairs of magnetic detection coils arranged to intersect with each other in a lattice form.

6. An apparatus for measurement of a magnetic field, the apparatus comprising:

a magnetic detection coil including a plurality of second-order differential coils;

a superconducting quantum interference device to which magnetic signals detected by the magnetic detection coil are transmitted; and a device configured to differentiate the magnetic signals detected by the plurality of second-order differential coils, wherein the plurality of second-order differential coils includes at least two second-order differential coils arranged in parallel, spaced a predetermined distance apart from each other, and composed of at least one of a superconductor or a metal material, wherein each of the at least two second-order differential coils comprises at least respective first, second, and third coils arranged in this order, wherein the respective first coil and the respective third coil of each second-order differential coil have mutually identical loop directions, wherein the respective second coil and the respective first coil of each second-order differential coil have mutually different loop directions, wherein the respective second coil and the respective third coil of each second-order differential coil have mutually different loop directions, wherein the respective first coil of a first second-order differential coil of the at least two second-order differential coils and the respective second coil of a second second-order differential coil of the at least two second-order differential coils have mutually identical loop directions, wherein the respective second coil of the first second-order differential coil of the at least two second-order differential coils and the respective first coil of the second second-order differential coil of the at least two second-order differential coils have mutually identical loop directions, and wherein the magnetic detection coil detects a magnetic flux that is based on a difference between a first magnetic flux penetrating the first second-order differential coil and a second magnetic flux penetrating the second second-order differential coil.

* * * * *